(12) United States Patent
Defaye et al.

(10) Patent No.: US 7,632,941 B2
(45) Date of Patent: Dec. 15, 2009

(54) CYCLODEXTRIN DERIVATIVES, METHOD FOR THE PREPARATION THEREOF AND USE THEREOF FOR THE SOLUBILIZATION OF PHARMACOLOGICALLY ACTIVE SUBSTANCES

(75) Inventors: Jacques Defaye, Saint-Ismier (FR); Carmen Ortiz-Mellet, Seville (ES); José Manuel Garcia-Fernandez, Seville (ES); Maria Gomez-Garcia, Seville (ES); Kazimierz Chmurski, Varsovie (PL); Jian-Xin Yu, Dallas, TX (US)

(73) Assignees: Centre National de la Recherche Scientifique, Paris (FR); Universite Joseph Fourier, Saint-Martin-d'Heres (FR); Consejo Superior de Investigaciones Cientificas (CSIC), Mardid (ES); Universidad de Sevilla, Seville (ES)

( * ) Notice: Subject to any disclaimer, the term of this patent is extended or adjusted under 35 U.S.C. 154(b) by 168 days.

(21) Appl. No.: 10/551,343

(22) PCT Filed: Mar. 22, 2004

(86) PCT No.: PCT/FR2004/000691

§ 371 (c)(1),
(2), (4) Date: Nov. 22, 2006

(87) PCT Pub. No.: WO2004/087768

PCT Pub. Date: Oct. 14, 2004

(65) Prior Publication Data

US 2007/0167401 A1  Jul. 19, 2007

(30) Foreign Application Priority Data

Mar. 28, 2003 (FR) .................................. 03 03899

(51) Int. Cl.
  *C08B 37/16* (2006.01)
  *C07H 1/00* (2006.01)
  *C07H 3/00* (2006.01)
  *C08B 37/00* (2006.01)
  *A01N 43/04* (2006.01)
  *A61K 31/715* (2006.01)

(52) U.S. Cl. .......................... 536/103; 536/124; 514/58

(58) Field of Classification Search ...................... None
See application file for complete search history.

(56) References Cited

FOREIGN PATENT DOCUMENTS

| WO | WO 95/19994 | 7/1995 |
|---|---|---|
| WO | WO 97/33919 | 9/1997 |
| WO | WO 98/05689 | 2/1998 |
| WO | WO 99/19994 | 4/1999 |
| WO | WO 99/45032 | 9/1999 |

OTHER PUBLICATIONS

Mellet et al. Chem. Eur. J. 2002, 8, No. 9, pp. 1982-1990.*
Yasuda et al. Chemistry Letters 2000, pp. 706-707.*
Nagata Y. et al.:, pH-Responsive Guest Binding of Polypeptide Containing a Cyclodextrin at the Terminal, Bull. Chem. Soc. Jpn. ol. 67, 1994, pp. 495-499, XP0001161089, p. 495, colonne de droite, ligne 23-ligne 41.
Nobuyoshi Aoki et al., "Gas chromatographic-mass spectrometric study of reactions of halodeoxycellulose with thiols in aqueous solutions", Carbohydrate Polymers, vol. 27, 1995 pp. 13-21, XP004034456, Great Britain, p. 15, colonne de gauche, ligne 15-ligne 17PA.
Juan J. Garcia-Lopez et al., "Synthesis of cluster N-Glycosides based on a beta-cyclodextrin core", Chem. Eur. Journal, vol. 5, No. 6. 1999, pp. 1775-1784, XP00828759, Weinheim, p. 1775, colonne de droite, dernier alinea p. 1778.

* cited by examiner

*Primary Examiner*—Shaojia Anna Jiang
*Assistant Examiner*—Layla Bland
(74) *Attorney, Agent, or Firm*—Young & Thompson

(57) ABSTRACT

The invention relates to a cyclodextrin derivative corresponding to general formula (I) wherein n is a whole number from 1-6, m is a whole number equal to 5, 6 or 7, $R^1$ is an OH group, all $R^1$s are identical, Z is a thiourea group, X is a hydrogen atom, and R is a hydrogen atom or a bioidentification element.

23 Claims, 1 Drawing Sheet

Figure 1:
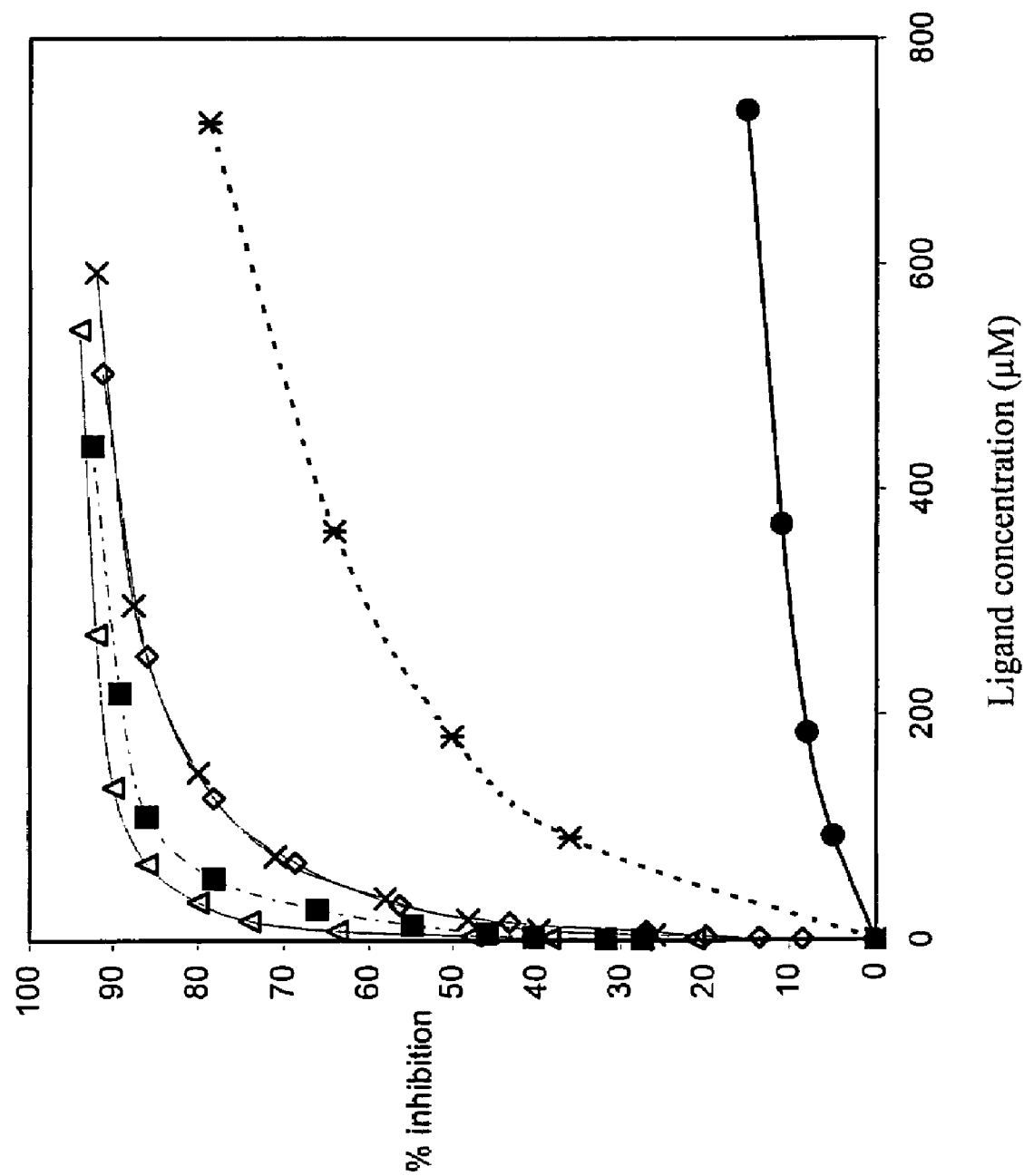

CYCLODEXTRIN DERIVATIVES, METHOD FOR THE PREPARATION THEREOF AND USE THEREOF FOR THE SOLUBILIZATION OF PHARMACOLOGICALLY ACTIVE SUBSTANCES

BACKGROUND OF THE INVENTION

1. Field of the Invention

The present invention relates to novel derivatives of cyclodextrins, as well as their preparation process. The present invention also relates to the use of these novel derivatives for solubilizing pharmacologically active substances in an aqueous medium.

2. Description of the Related Art

Cyclodextrins, or cyclomaltooligosaccharides, are cyclic oligosaccharides which are known for their ability to contain various molecules in their cavity, of a size which is suited to that of the host structure. The generally apolar character of these associations preferably leads to the inclusion of molecular structures of the hydrophobic type, in particular allowing the solubilization in water and biological media of compounds which are slightly or not at all soluble in these media and optionally improvement of their stabilization. These properties are currently used in particular for the transport of medicaments.

However the relatively poor solubility in water of cyclodextrins, and in particular of the most accessible of them in terms of cost, β-cyclodextrin (18 g/l, i.e. 15 mmol/l, at 25° C.) limits their use for this purpose. In addition, because cyclodextrins do not have the capacity to recognize biological receptors in the organism, these entities cannot be used for the targeting and vectorizing of active ingredients.

In order to remedy this situation, cyclodextrins have been chemically modified in order to improve their solubility in water on the one hand and, on the other hand, in order to incorporate in their structure cell recognition signals. Thus, the international applications WO 95/19994, WO 95/21870 and WO 97/33919 and the European Patent Application EP 0 403 366 describe cyclodextrin derivatives in which one or more primary alcohol functions are substituted by monosaccharide or oligosaccharide groups via an oxygen or sulphur atom or via a thiourea group, as well as their use. These branched cyclodextrins are in particular able to serve as a host for taxol and its derivatives, in particular Taxotere®, which are antineoplastic and antiparasitic agents, as described by P. Potier in $Chem.\ Soc.\ Rev.,$ 21, 1992, pp. 113-119. Inclusion complexes are thus obtained which allows these antineoplastic agents to be solubilized in water. By way of example, the solubility in water of Taxotere® which is 0.004 g/l, can be increased up to 6.5 g/L by adding $6^I$-S-α-maltosyl-$6^I$-thiocyclomaltoheptaose to its aqueous suspension, as described in the document WO 95/19994.

The document EP-A-0 605 753 describes taxol inclusion complexes using branched cyclodextrins such as maltosyl-cyclodextrins, in order to increase the solubility of this compound in water.

Cyclodextrin derivatives comprising one or more glycosyl or maltosyl substituents linked to cyclodextrin by a sulphur atom are also described by V. Lainé et al. in $J.\ Chem.\ Soc.,\ Perkin\ Trans.,$ 2, 1995, pp. 1479-1487. These derivatives were used to solubilize an anti-inflammatory drug such as prednisolone.

The document WO 97/33919 describes the processes for the preparation of thioureido-cyclodextrins by coupling of $6^I$-amino-$6^I$-deoxycyclodextrins or also of the corresponding peraminated derivatives with alkyl isothiocyanates or mono- or oligosaccharides.

The incorporation of glucidic substituents on the cyclodextrins leads to derivatives endowed with a solubility in water which is much greater compared to the starting cyclodextrin. At the same time, this approach allows the cyclodextrin to have a particular affinity for certain biological sites, because the glucidic substituents are well known as cell recognition markers. Thus, this type of modification of cyclodextrin can allow the targeting and vectorizing of an active substance included in the cyclodextrin.

The affinity of a glucidic marker for a specific cell membrane receptor (lectin) is generally poor. In order to obtain affinities which are useful for targeting and vectorizing, a multiple and simultaneous presentation of the ligand must be envisaged. In the case of cyclodextrin derivatives monosubstituted in primary alcohol position (i.e. cyclodextrins in which one of the OH groups of primary alcohol is substituted), this problem can be partially resolved by the incorporation of glycerophtalic structures, as described by I. Baussanne et al. in $Chem.\ Commun,$ 2000, pp. 1489-1490. However, the preparation process of such compounds is complicated.

Moreover, the recent results described by I. Baussanne et al. in $ChemBioChem$ 2001, pp. 777-783 show that the derivatives of β-cyclodextrin comprising substituents of the glycosylthioureido type, obtained from the corresponding per-(C-6)-amine, do not demonstrate sufficient affinity for complementary lectins.

At present, there exists no mono or polysubstituted cyclodextrin derivative, which is obtained by a simple process, allowing an increase in the solubilization of pharmacologically active substances and also having sufficient affinity for complementary lectins.

BRIEF SUMMARY OF THE INVENTION

One of the aims of the present invention is to provide novel cyclodextrin derivatives, polysubstituted but also monosubstituted, in primary alcohol position, having not only an advantage for the solubilization of the active substances, in particular of the antineoplastic drugs of the taxol family such as Taxotere®, but also a strong affinity for specific membrane receptors, which allows an effective and selective transport of the active substance to the targeted organs by means of these derivatives to be envisaged.

One of the aims of the invention consists of providing a preparation process which is easy to implement, and making it possible to obtain novel cyclodextrin derivatives with a good yield of the order of at least 50%, and preferably 70%, without having to carry out long and complicated purifications.

DETAILED DESCRIPTION OF THE PREFERRED EMBODIMENTS

The present invention relates to the use of a process comprising a stage of reaction of a compound selectively or totally halogenated in primary alcohol position, of the following formula (VII):

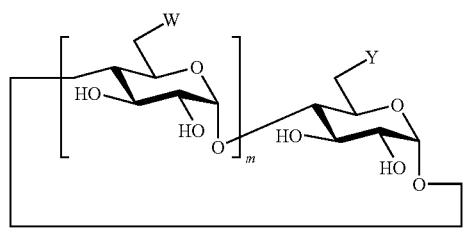

(VII)

m representing an integer equal to 5, 6 or 7,

W representing an OH group or a Y group, the W groups all being identical, and Y representing a halogen atom chosen from the group constituted by chlorine, bromine, iodine, and preferably being bromine or iodine, with an ω-aminoalkanethiol of the following formula (VIII):

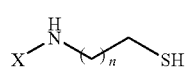

(VIII)

said ω-aminoalkanethiol being optionally N-alkylated, or the corresponding salt of the following formula (VIII-a):

(VIII-a)

or a tetraalkylammonium salt of the following formula (VIII-b):

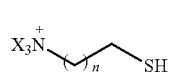

(VIII-b)

said salt being associated with a halide counter ion, preferably the chloride ion, n representing an integer from 1 to 6, X representing a hydrogen atom or an alkyl group comprising from 1 to 6 carbon atoms, and being in particular a methyl, ethyl, propyl or butyl group, X preferably being a hydrogen atom, the compound of formula (VIII) preferably being cysteamine of formula $H_2N-CH_2-CH_2-SH$, in order to obtain a compound having the following formulae (A-a) or (A-b):

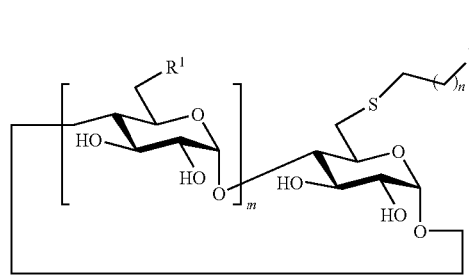

(A-a)

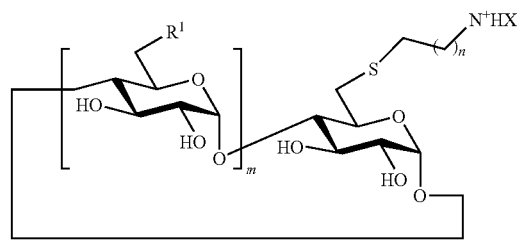

(A-b)

$R_1$ representing either an OH group or an $-S-CH_2-(CH_2)_n-Z$ group, the $R^1$ groups all being identical, Z representing an NHX group or a quaternary ammonium group of the $^+NX_3$ form, m, n and X being as defined above, for the preparation of compounds of the following formula (I):

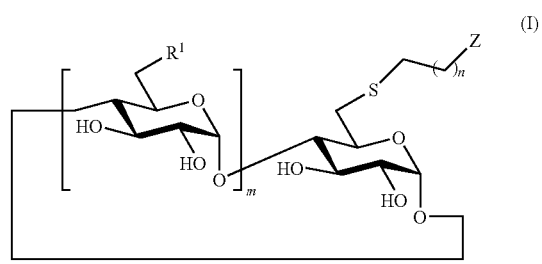

(I)

in which:

m, n and $R_1$ are as defined above, and

Z represents either:

an NHX group, a quaternary ammonium group of the $^+NX_3$ form, a

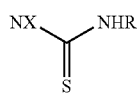

group,

X being as defined above, and

R representing a hydrogen atom, a linear or branched alkyl substituent with 1 to 12 carbon atoms, or an aromatic group such as the phenyl, benzyl or naphthyl group, or derivatives of these groups carrying substituents on the aromatic ring such as methyl, ethyl, chlorine, bromine, iodine, nitro, hydroxyl, methoxyl or acetamido substituents, or R representing a biorecognition element such as an amino acid derivative, a peptide, a monosaccharide, an oligosaccharide, a multiplication element with several branchings comprising glucidic groups which can be identical or different, or a visualization probe or fluorescent or radioactive detection probe.

The present invention relates to a compound having the following general formula:

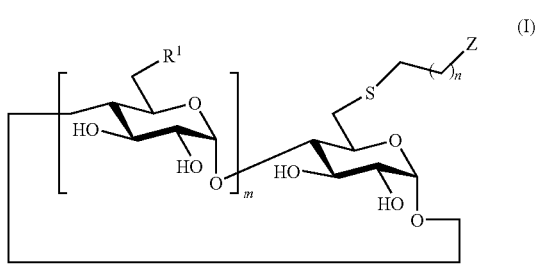

in which:
n represents an integer from 1 to 6;
m represents an integer equal to 5, 6 or 7;
$R^1$ represents either an OH group or an —S—CH$_2$—(CH$_2$)$_n$—Z group, the $R^1$ groups all being identical;
Z represents either:
an NHX group,
a quaternary ammonium group of the $^+$NX$_3$ form,
a

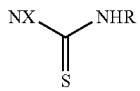

group,
X representing a hydrogen atom or an alkyl group comprising from 1 to 6 carbon atoms, and being in particular a methyl, ethyl, propyl or butyl group, and
R representing a hydrogen atom, a linear or branched alkyl substituent with 1 to 12 carbon atoms, or an aromatic group such as the phenyl, benzyl or naphthyl group, or derivatives of these groups carrying substituents on the aromatic ring such as methyl, ethyl, chlorine, bromine, iodine, nitro, hydroxyl, methoxyl or acetamido substituents,
or R representing a biorecognition element such as an amino acid derivative, a peptide, a monosaccharide, an oligosaccharide, a multiplication element with several branchings, which branchings comprise glucidic groups which can be identical or different, or a visualization probe or fluorescent or radioactive detection probe, provided that the compound in which n=1, m=6, Z=NH$_2$ and R$_1$=OH is excluded.

The expression "biorecognition element" designates a molecular structure complementing a biological receptor, which can be recognized by the latter and can lead to a specific response: induction and regulation of the biosynthesis of an enzyme, inhibition of the activity of an enzyme by binding on its active site, induction of an immune response following a bacterial disease, inhibition of an inflammatory process by blocking the active site of a selectin, etc.

The expression "multiplication element with several branchings" designates in particular a branched carbon chain comprising a tetrasubstituted quaternary carbon such as the derivatives of tris(2-aminomethyl)methylamine (TRIS) and of pentaerythritol.

The expression "visualization probe or fluorescent or radioactive detection probe" designates a molecular structure allowing the detection of a system by a physico-chemical technique, such as fluorescence or radioactivity. Among the fluorescent probes, there can be mentioned in particular the derivatives of fluorescein, dansyl (5-(dimethylamino)-1-naphthalenesulphonyl) or coumarin. Among the radioactive probes, there can be mentioned the products marked with a radioisotope.

Formula (I) mentioned above relates both to compounds which are poly- and monosubstituted on the cyclodextrin ring. The monosubstituted compounds correspond to formula (I) in which $R^1$ represents OH and the polysubstituted compounds correspond to formula (I) in which $R^1$ represents —S—CH$_2$—(CH$_2$)$_n$—Z.

In these novel derivatives, it has been found that the presence of a spacer group of the cysteaminyl type or, more generally, of a spacer group derived from a ω-aminoalkanethiol, between the primary alcohol position of the cyclodextrin and the Z group, is advantageous, in particular on the one hand in order to increase the reactivity of the amine groups in the case of the compounds corresponding to formula (I), Z representing NHX, and on the other hand in order to guarantee the effectiveness of the phenomenon of cell recognition in the case of the derivatives having the formula (I), Z representing a thiourea group. Moreover it is to be noted that this spacer group is easily introduced using commercial cysteamine or the corresponding ω-aminoalkanethiol homologue as reagent, which avoids in particular the stage of reduction required when the amine groups are prepared from a precursor of the azide type as is the case in the examples described in the document WO 97/33919 mentioned above.

It is to be noted that the product of formula (I) in which m is equal to 6, R$_1$ represents OH and Z represents NH$_2$ was prepared previously by reaction of the 6$^I$-O-tosylcyclomaltoheptaose in N,N-dimethylformamide with cysteamine at ambient temperature with a yield which is not specified (Y. Nagata et al., *Bull Chem. Soc. Jpn.* 1994, 67, 495-499) or also by reaction of this tosylate with cysteamine hydrochloride in a water-dimethylformamide mixture at 60° C. in the presence of sodium hydrogen carbonate with a yield of 43% (B. Ekberg et al., *Carbohydr. Res.*, 1992, 192, 111-117). In the context of the present invention, this product was used as a synthesis intermediate in order to obtain the corresponding thioureido cysteaminyl cyclodextrins. It was found to be advantageous to prepare it by reaction of a C-6 monohalogenated precursor of β-cyclodextrin, preferably bromide, with cysteamine hydrochloride in N,N-dimethylformamide in the presence of triethylamine (yield 85%). Optionally, the amine group of cysteamine or of ω-aminoalkanethiol can carry an alkyl substituent such as a methyl, ethyl, propyl or butyl group. This prefunctionalized spacer group allows the cyclodextrin to be associated with a hydrophilic and cell recognition unit such as a glucidic derivative, or also an amino acid or a peptide, via bonds of the thiourea, amide and thioether type which are very stable and produce well defined structures. The thiourea bond is created in a last stage and allows the cyclodextrin to be coupled to numerous substituents, in particular substituents comprising a multiplication element with several branchings, said branchings containing various glucidic units or even a visualization probe or a fluorescent or radioactive detection probe.

The cysteaminyl-cyclodextrins of formula (I) given above in which Z represents an amine group of the NHX type (X=H or alkyl substituent) can be isolated in the form of an ammonium salt (in the case where Z represents $^+$NX$_3$) or a free base (in the case where Z represents NHX). In the case of the salt, the counter ion is a monovalent anion, in particular a halide such as chloride, bromide or iodide. This is in particular the case for the cysteaminyl-cyclodextrins corresponding to formula (I) in which Z represents a positively charged quaternary ammonium group, of the $^+$NX$_3$ type (X=alkyl substituent).

The compounds of formula (I), in which Z represents NHX, can be used as precursors in the preparation of thioureidocysteaminyl-cyclodextrins, in particular of hyperbranched derivatives. When Z in formula (I) represents an $NH_2$ group, the thioureas obtained are N,N'-disubstituted, whereas when Z represents an NHX group, X representing an alkyl substituent, such as methyl, ethyl, propyl or butyl, the thioureas obtained are N,N,N'-trisubstituted.

In the case of the thioureidocysteaminyl-cyclodextrins of formula (I), in which Z represents a thiourea group, the R substituents can be of various types. Thus, R can represent a hydrogen atom, a linear or branched alkyl substituent with 1 to 12 carbon atoms, or an aromatic group such as phenyl, benzyl, naphthyl or derivatives of these groups carrying substituents on the aromatic ring, said substituents being as defined previously. R can also in particular represent groups derived from optionally substituted amino acids, peptides, monosaccharides or oligosaccharides. By way of examples of groups derived from monosaccharides, there can be mentioned those derived from glucose, mannose and galactose, in an α or β anomeric configuration. In the case where the group derived from monosaccharide is substituted, one or more of the hydroxyl groups of the monosaccharide can be replaced by alkoxy groups with 1 to 16 carbon atoms, acyloxy groups such as the acetoxy group, amine and amide groups. The groups derived from oligosaccharides can be the maltosyl, maltotriosyl, lactosyl groups, or also tri- or tetrasaccharide cell affinity markers of the Lewis X or sialyl Lewis X type, or also oligosaccharides derived from heparin. They can also be substituted by alkoxy, acyloxy groups, aminated, sulphated or phosphated groups.

According to the invention, R can also represent a group comprising a branched multiplication element, for example a group derived from tris(2-hydroxymethyl)methylamine (TRIS) or from pentaerythritol, comprising in the branchings groups derived from mono- or oligosaccharides which can be identical or different. By way of examples, there can be mentioned the groups derived from mono- or oligosaccharides already mentioned in the preceding paragraph, which can also comprise oxygenated or aminated substituents. These glucidic groups can be linked to the multiplication element via an oxygenated, sulphurated or aminated bond. In the case where R comprises a branching element, one of the branchings can also carry a fluorescent type probe, in particular a derivative of fluorescein or also a radioactive probe.

According to an advantageous embodiment, the compounds of the invention have one of the following formulae:

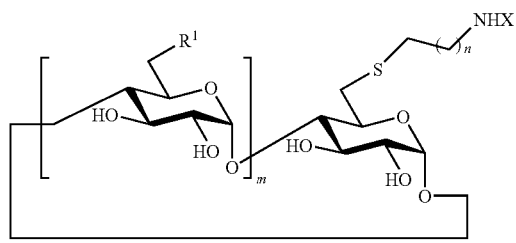

(A-a)

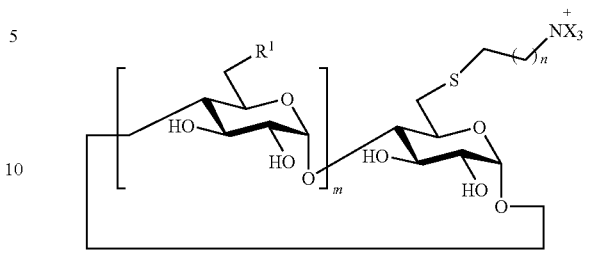

(A-b)

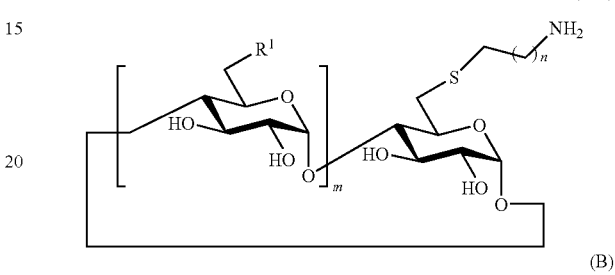

(A-c)

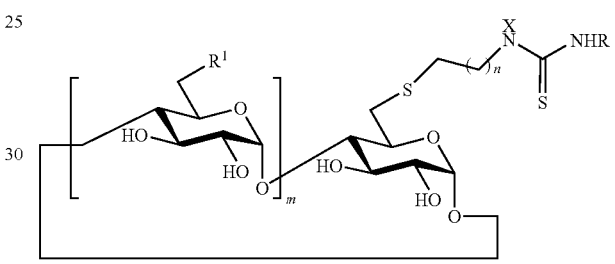

(B)

in which m, n, $R^1$, X and R are as defined previously.

An advantageous compound of the present invention is characterized in that $R^1$ represents OH, and has the following general formula:

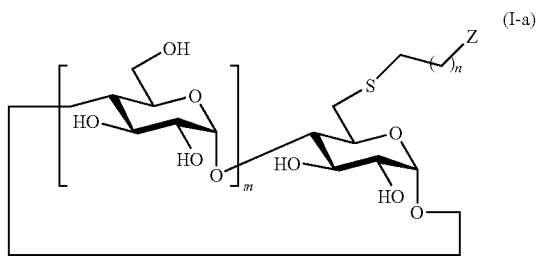

(I-a)

in which:

m, n and Z are as defined above.

The compounds mentioned above are compounds monosubstituted on the cyclodextrin ring.

In this type of compound, the access to the cavity of the cyclodextrin is less encumbered than in the case of the compounds of the prior art, which can result in better complexing properties for certain guest molecules.

An advantageous compound of the present invention, having the formula (I-a), is characterized in that Z represents an NHX group, X being as defined above, and in particular being a hydrogen atom.

Such compounds have the following formula:

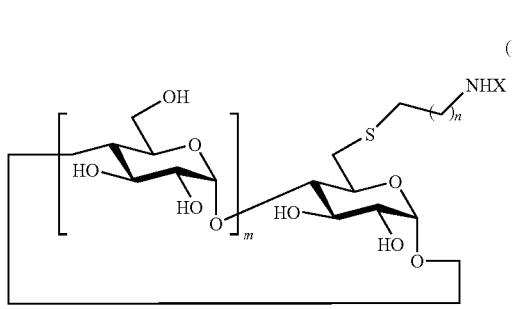
(I-f)

The compounds mentioned above can serve as reaction intermediates when X represents a hydrogen atom, in order to obtain the compounds of formula (I-a) in which Z represents a thiourea group.

An advantageous compound of the present invention, having the formula (I-a), is characterized in that Z represents an $NH_2$ group or an $NX_3^+$ group and has one of the following formulae (I-f-bis) or (I-g):

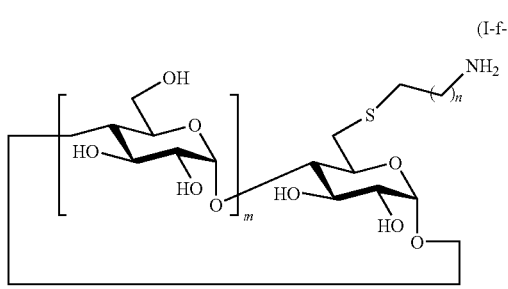
(I-f-bis)

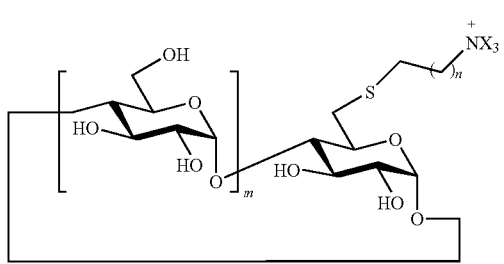
(I-g)

in which m, n and X are as defined previously.

An advantageous compound according to the present invention is a compound as defined above, corresponding to formula (I-a) and characterized in that Z represents a

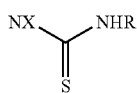

group, R being as defined above, and X being as defined above, and in particular being a hydrogen atom.

Such compounds have the following formula:

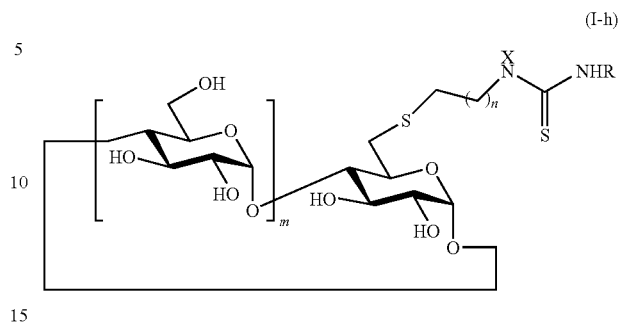
(I-h)

An advantageous compound according to the present invention is a compound of formula (I) as defined above, characterized in that $R^1$ represents an $-S-CH_2-(CH_2)_n-Z$ group, and having the following general formula (I-b):

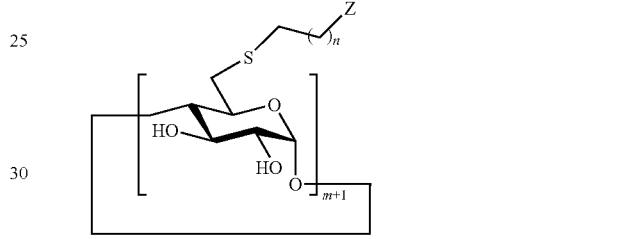
(I-b)

in which m, n and Z are as defined above.

The compounds mentioned above are compounds polysubstituted on the cyclodextrin ring.

In such structures, the incorporated biorecognition elements are multiplied compared to the monosubstituted derivatives, which, in the case of the compounds of the invention, can result in better affinities for the biological receptors. For the hyperbranched derivatives, new supramolecular (therefore transport) properties can be envisaged due to the possibility of extension of the cyclodextrin cavity by C-6 substituents.

An advantageous compound according to the present invention is a compound as defined above, of formula (I-b), having the following formula:

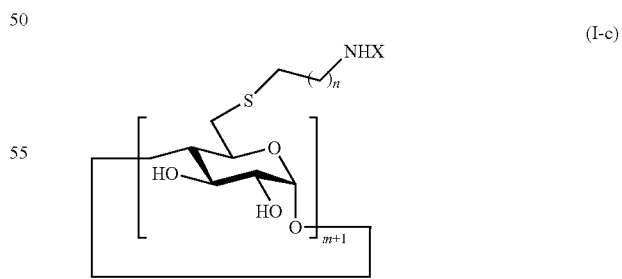
(I-c)

X, n and m being as defined above.

The compounds of formula (I-c) are compounds derived from cyclodextrin, called cysteaminylcyclodextrin compounds, and can serve as reaction intermediates, when X represents a hydrogen atom, in order to obtain the compounds of formula (I-b) in which Z represents a thiourea group.

An advantageous compound according to the present invention is a compound as defined above, of formula (I-b), characterized in that X represents a hydrogen atom and in that n is equal to 1, and having the following formula:

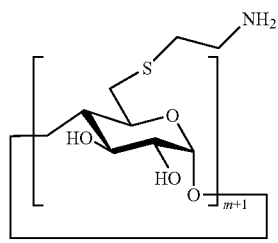

(I-d)

m being as defined above.

An advantageous compound according to the present invention is a compound as defined above, of formula (I-b), having the following formula:

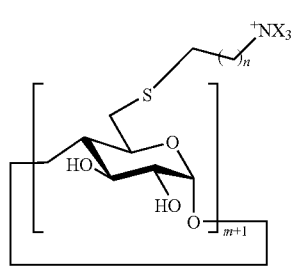

(I-e)

X, n and m being as defined above.

An advantageous compound according to the present invention is a compound as defined above, which corresponds to the following formula (II):

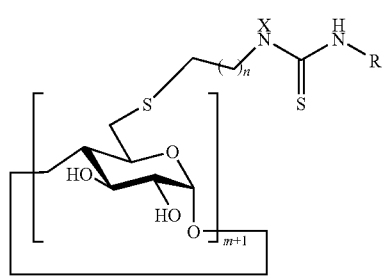

(II)

X, n, m and R being as defined above, and R being identical for each

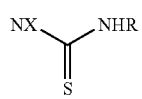

group as defined above.

The compounds of formula (II) are compounds derived from cyclodextrin, called thioureidocysteaminyl-cyclodextrin compounds.

An advantageous compound according to the present invention is a compound as defined above, of formula (II), characterized in that X represents a hydrogen atom and in that n is equal to 1, and having the following formula:

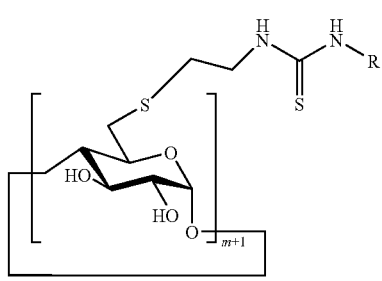

(II-a)

R and m being as defined above.

An advantageous compound according to the present invention is a compound as defined above, characterized in that at least one of the NHX groups as defined above is protonated and associated with a monovalent anion chosen in particular from the chloride, bromide or iodide ion.

The present invention also relates to a compound as defined above, characterized in that n is equal to 1 and in that the Z group represents the quaternary ammonium $^+NX_3$ group, and in that it can be associated with a monovalent anion chosen in particular from the chloride, bromide or iodide ion, and corresponding to the following formula:

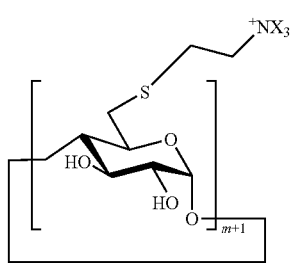

(I-e-bis)

These positively charged products can have favourable electrostatic interactions with negatively charged molecules such as polynucleotides. From this point of view, an application of these derivatives as vectors for gene transfer can be envisaged. Moreover, as described by J. Defaye et al. (*J. Incl. Phen. Mol. Recogn. Chem.* 29 (1997) 57-63), it is known that the presence of a positively charged group at the position C-6 of the cyclodextrins reduces the hemolytic character of these entities, and therefore their toxicity.

The present invention also relates to a compound of formula (II-a) as defined above, characterized in that the R group is chosen from the following groups:

the α-D-mannopyranosyl group, of the following formula (III):

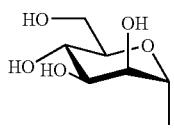

(III)

the β-lactosyl group, of the following formula (III-a):

(III-a)
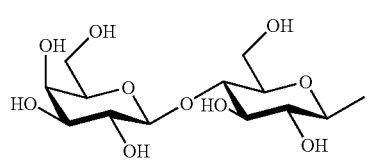

the group derived from Lewis X trisaccharide or from sialyl Lewis X tetrasaccharide, of the following formulae (III-b) and (III-c) respectively:

(III-b)
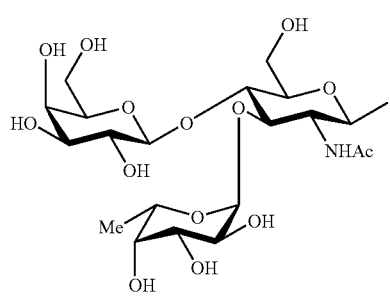

(III-c)
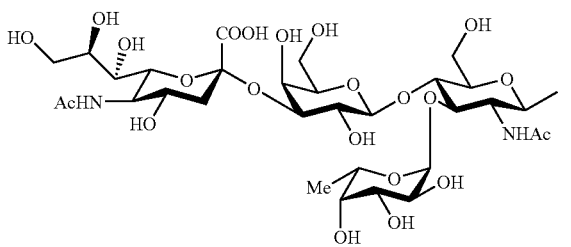

an oligosaccharide derived from heparin, of the following formula (III-d):

(III-d)
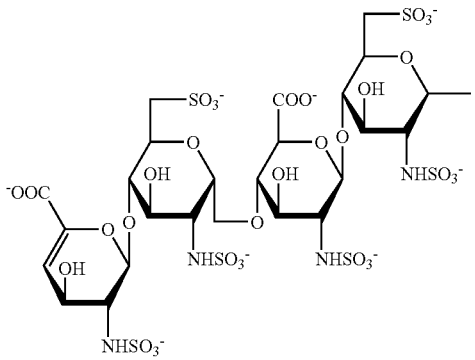

Thus, the present invention relates to the compounds having one of the following formulae:

compound of formula (II-a) when R represents the α-D-mannopyranosyl group of formula (III):

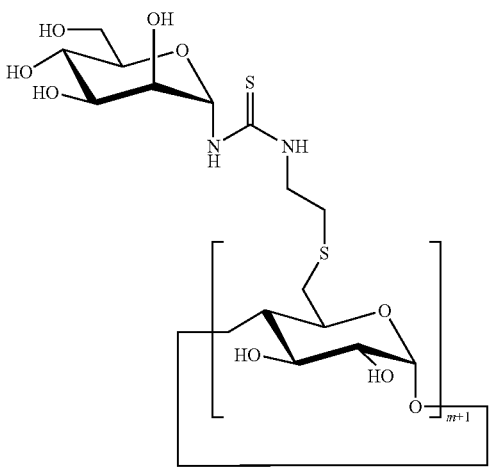

compound of formula (II-a) when R represents the β-lactosyl group of formula (III-a):

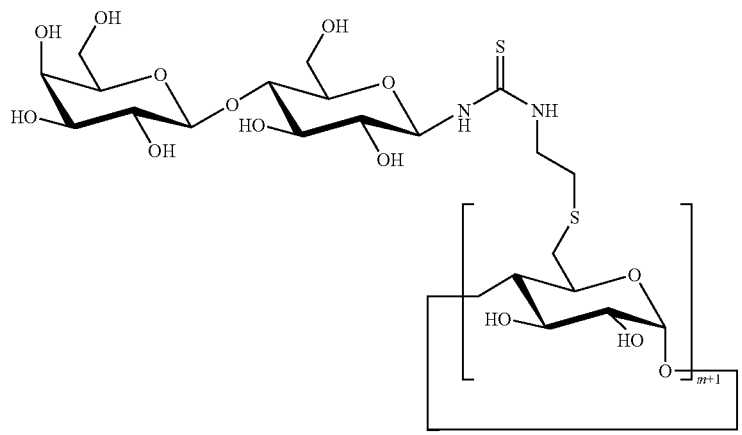

compound of formula (II-a) when R represents the group derived from Lewis X trisaccharide of formula (III-b):
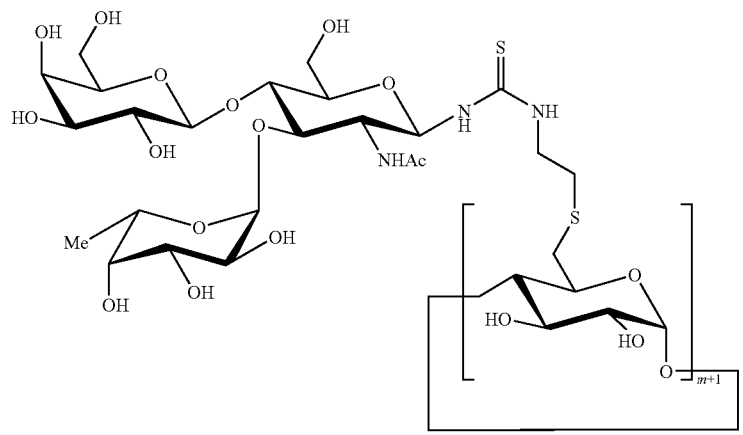
compound of formula (II-a) when R represents the group derived from sialyl Lewis X tetrasaccharide of formula (III-c):
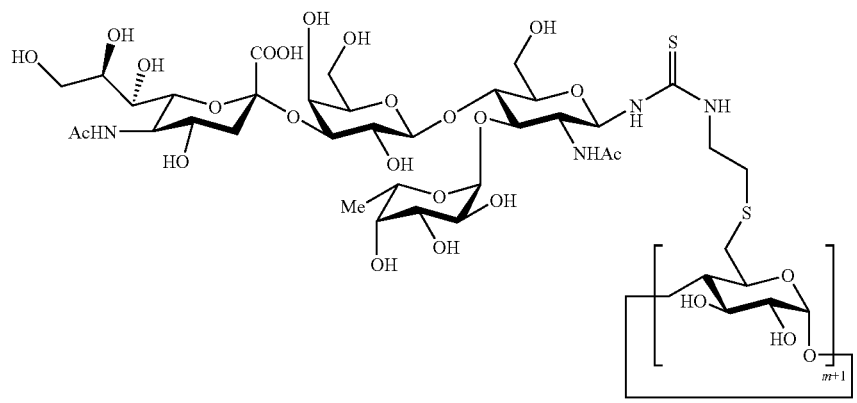
compound of formula (II-a) when R represents an oligosaccharide derived from heparin, of formula (III-d):
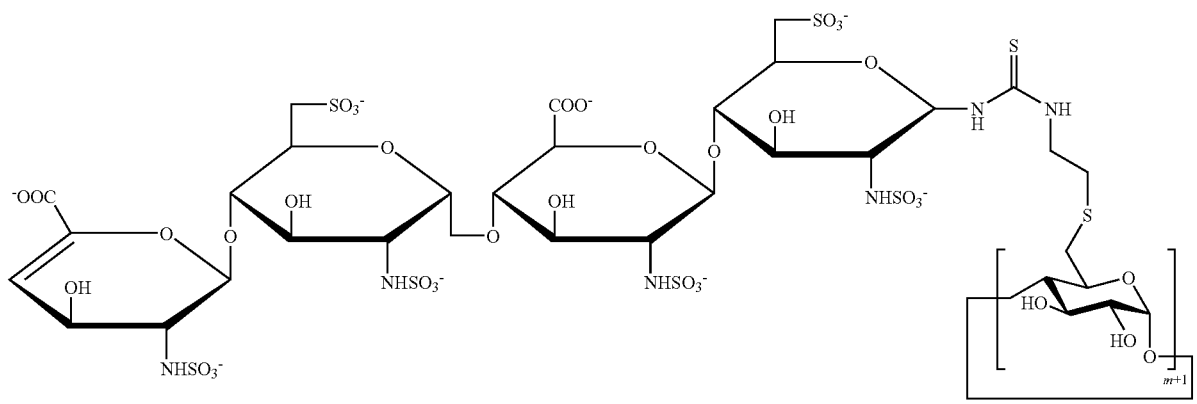

The present invention also relates to a compound of formula (II-a) as defined above, characterized in that:

R comprises a branching element derived from tris(2-hydroxymethyl)methylamine, or R represents one of the following groups:

the tris(α-D-mannopyranosyloxymethyl)methyl group, of the following formula (IV):

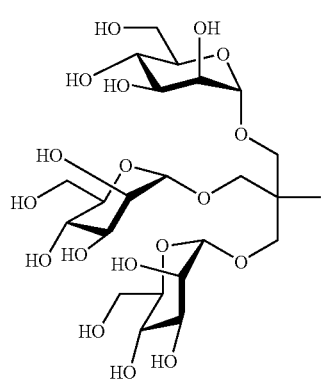

(IV)

the tris(β-lactosyloxymethyl)methyl group, of the following formula (IV-a):

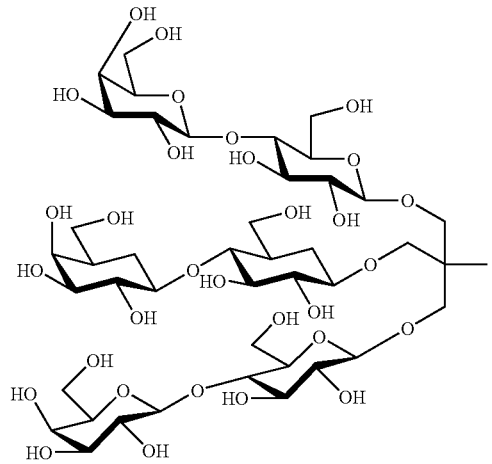

(IV-a)

The present invention also relates to the compounds having one of the following formulae:

compound of formula (II-a) when R represents the tris(α-D-mannopyranosyloxymethyl)methyl group, of formula (IV):

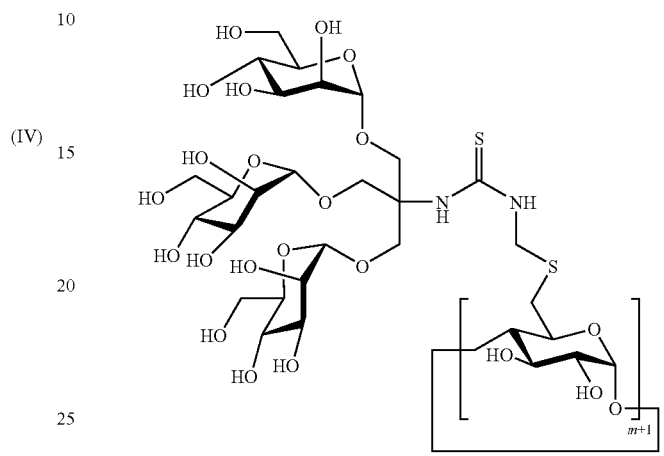

compound of formula (II-a) when R represents the tris(β-lactosyloxymethyl)methyl group, of formula (IV-a):

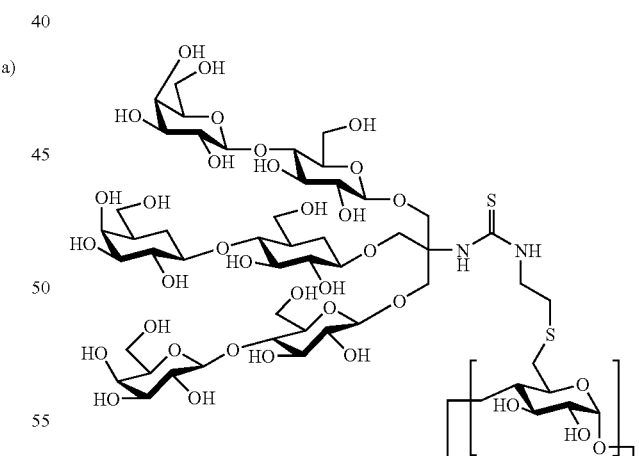

The present invention also relates to a compound of formula (I-a) as defined above, characterized in that R comprises a branching element derived from pentaerythritol, said compound having the following formula:

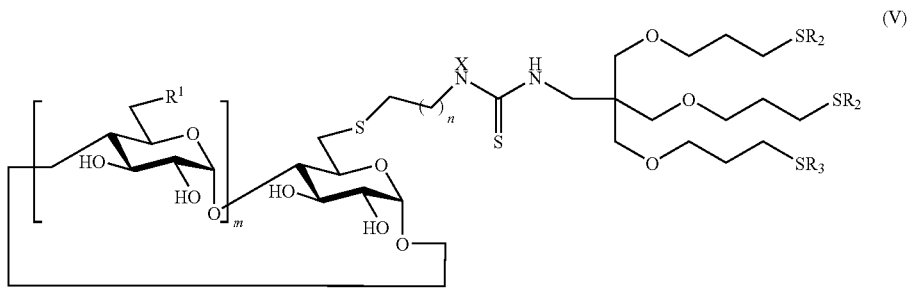

in which m, n, $R^1$ and X are as defined above, and $R^2$ and $R^3$ represent glucidic derivatives which can be different or identical or also a fluorescent or radioactive probe.

An advantageous compound according to the present invention is a compound as defined above, of formula (V), characterized in that $R^1$ represents OH.

Such a compound has the following formula:

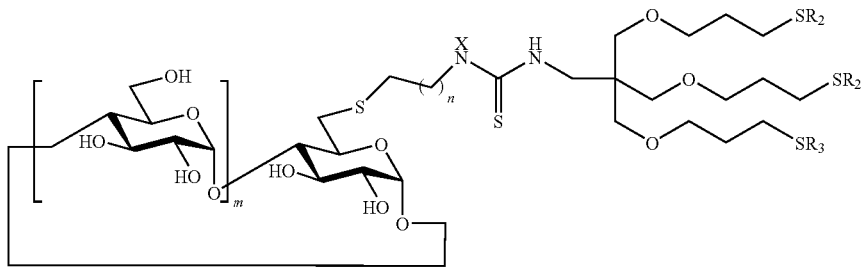

The compounds mentioned above represent compounds monosubstituted on the cyclodextrin ring.

An advantageous compound according to the present invention is a compound as defined above, of formula (V), characterized in that $R^1$ represents the group of formula:

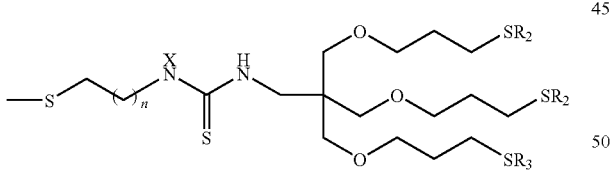

Such a compound has the following formula:

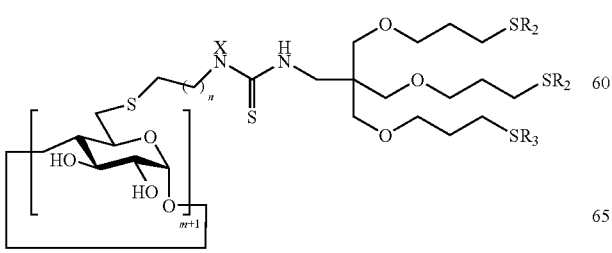

The compounds mentioned above represent compounds polysubstituted on the cyclodextrin ring.

The present inventions also relates to a compound as defined previously, of formula (V), characterized in that n is equal to 1, in that X represents a hydrogen atom, and in that $R_2$ and $R_3$ represent one of the following groups:

the α-D-mannopyranosyl group, of formula (III), as defined above, or the β-lactosyl group, of formula (III-a), as defined above, or the β-D-glucopyranosyl group, of the following formula (VI):

$R^2$ and $R^3$ being able to be identical or different.

Such compounds have one of the following formulae:

a) Monosubstituted compounds (in the case where $R_1$ represents OH)

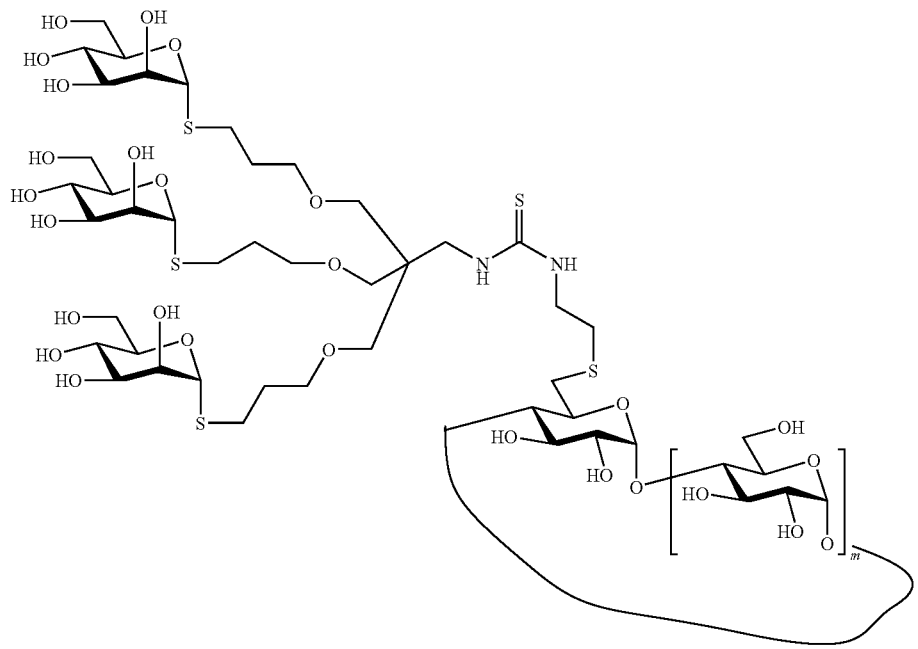
(V; R$_2$ = R$_3$ = α-D-mannopyranosyl)
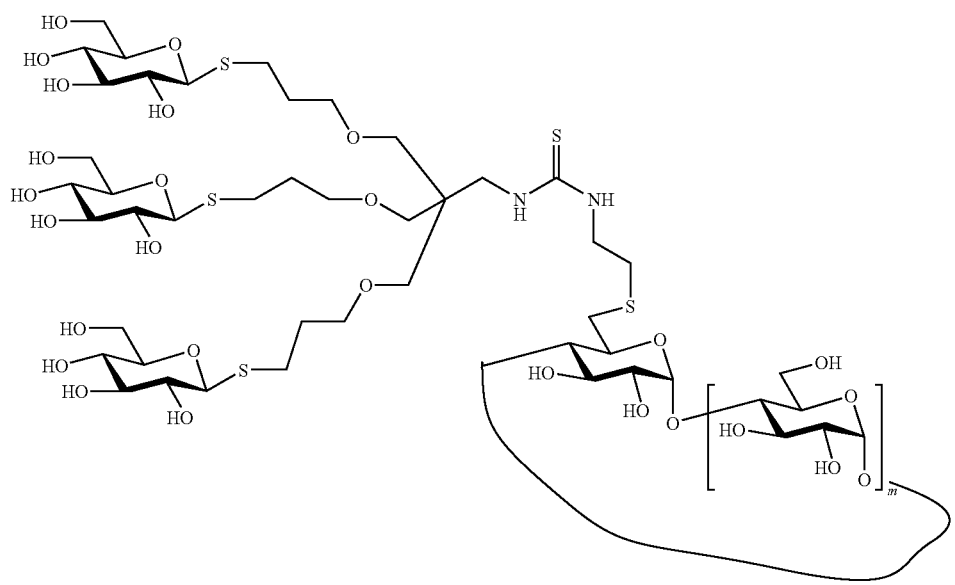
(V; R$_2$ = R$_3$ = β-D-glucopyranosyl)

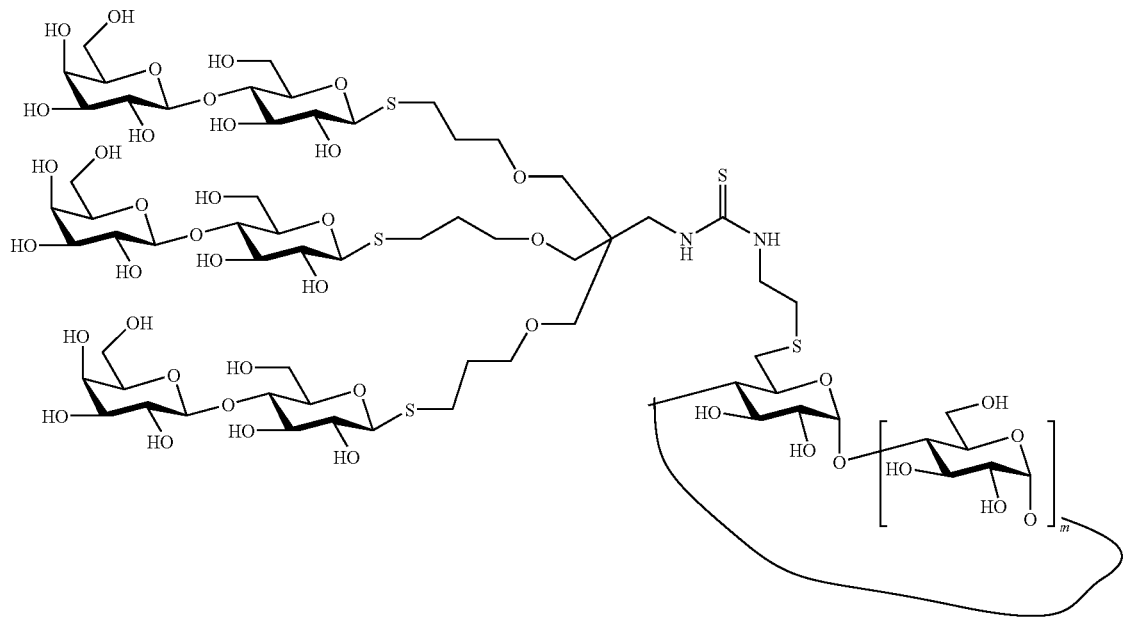
(V; R₂ = R₃ = β-lactosyl)
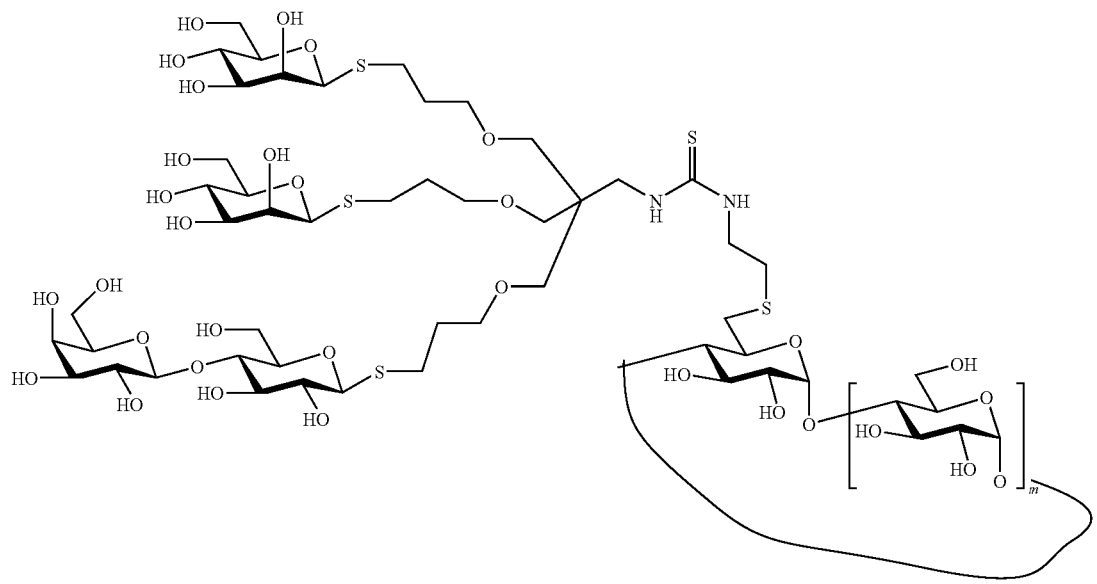
(V; R₂ = α–D-mannopyranosyl; R₃ = β-lactosyl)

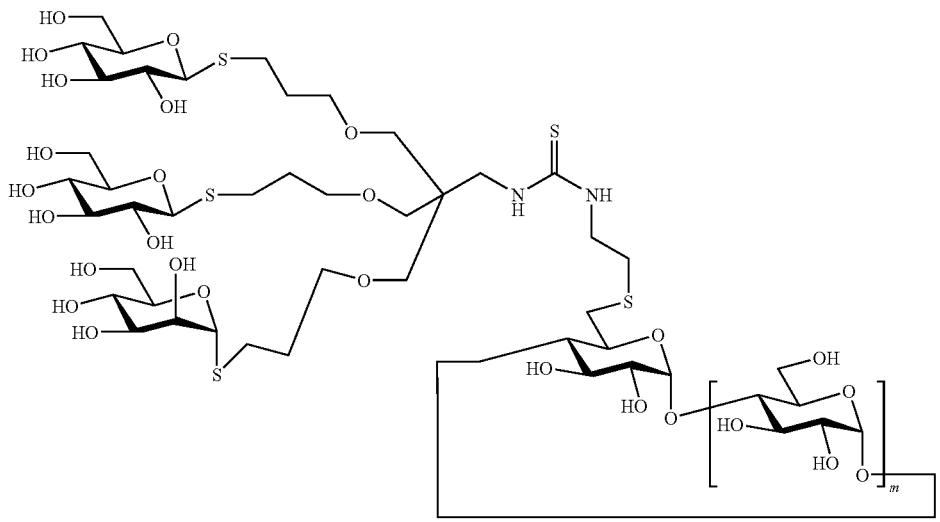
(V; R$_2$ = β–D-glucopyranosyl; R$_3$ = α-D-mannopyranosyl)
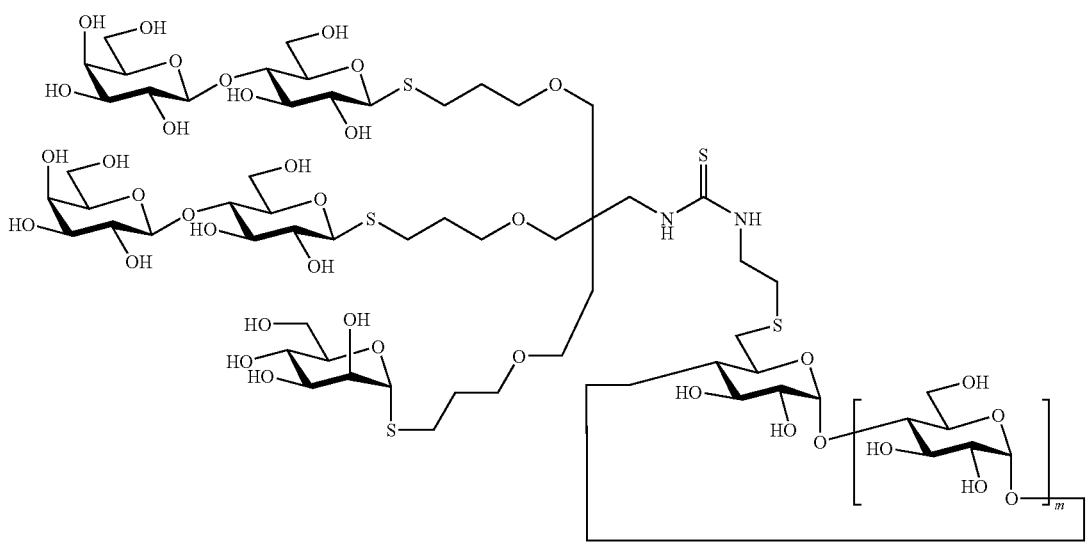
(V; R$_2$ = β–lactosyl; R$_3$ = α-D-mannopyranosyl)

-continued
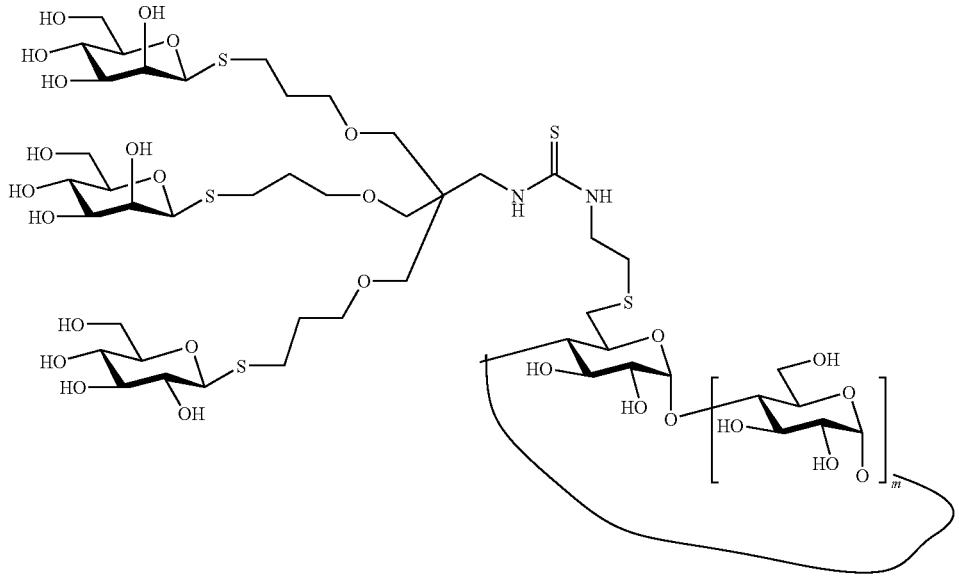
(V; $R_2$ = α–D-mannopyranosyl; $R_3$ = β-D-glucopyranosyl)
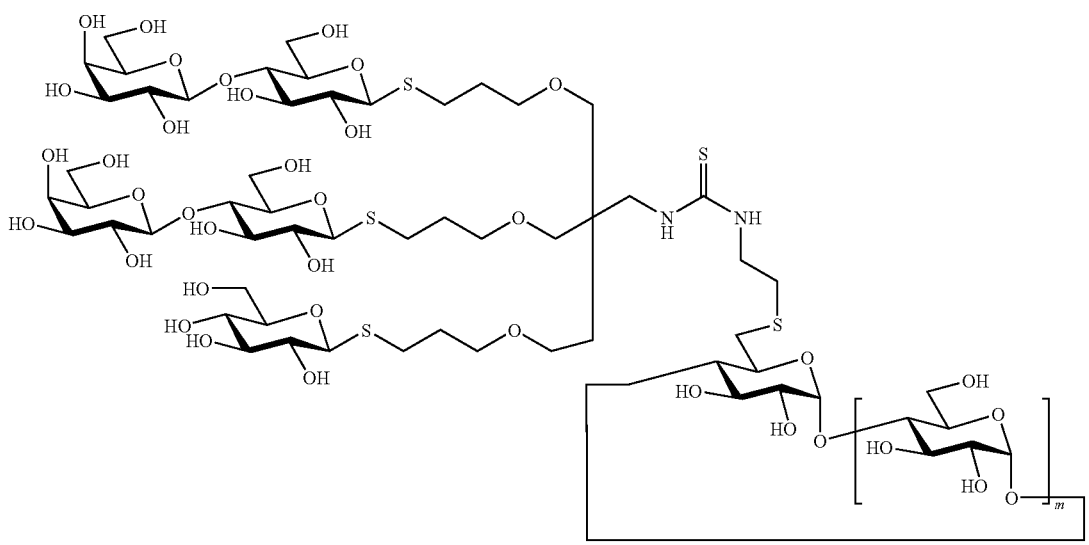
(V; $R_2$ = β–lactosyl; $R_3$ = β-D-glucopyranosyl)

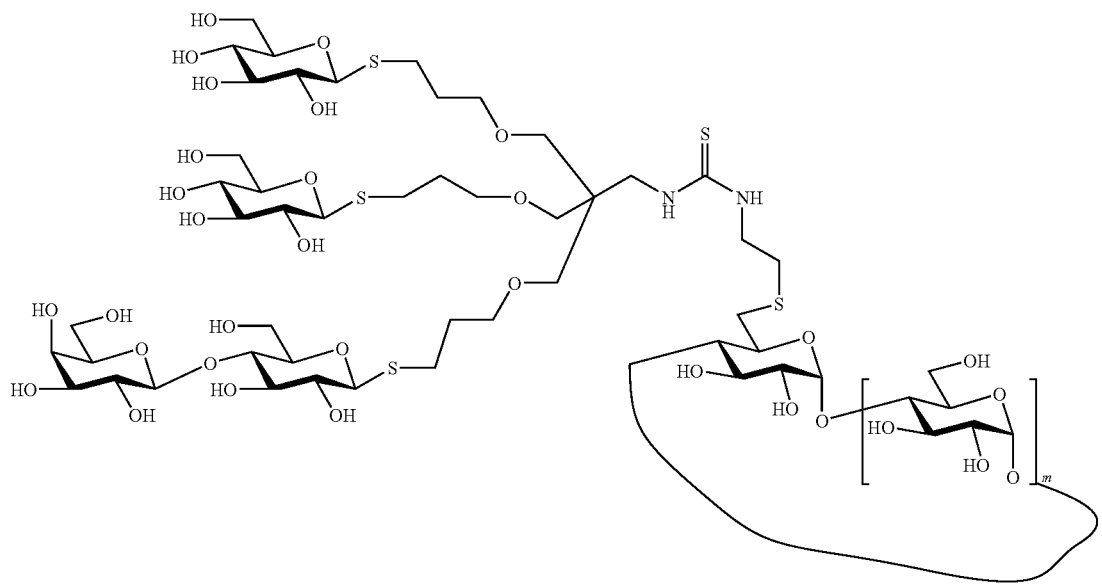
(V; R₂ = β-D-glucopyranosyl; R₃ = β-lactosyl)
b) Polysubstituted Compounds
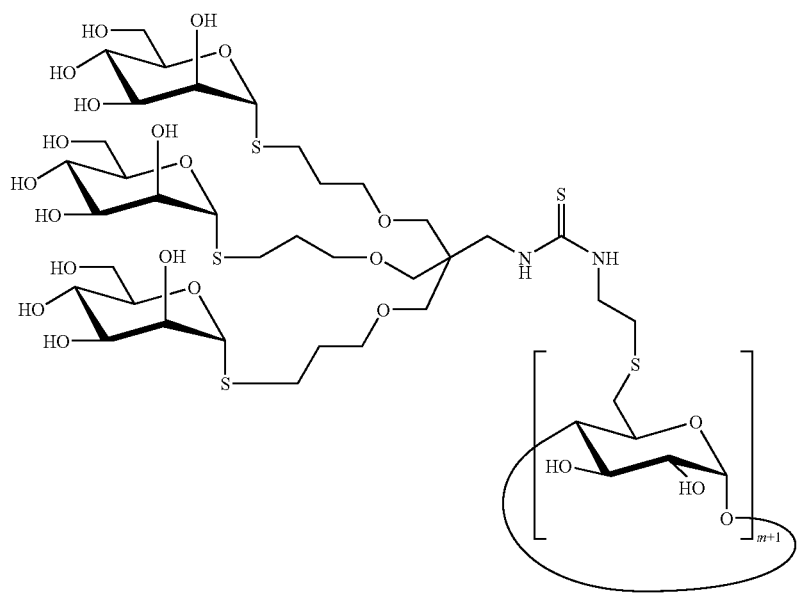
(V; R₂ = R₃ = α-D-mannopyranosyl)

-continued
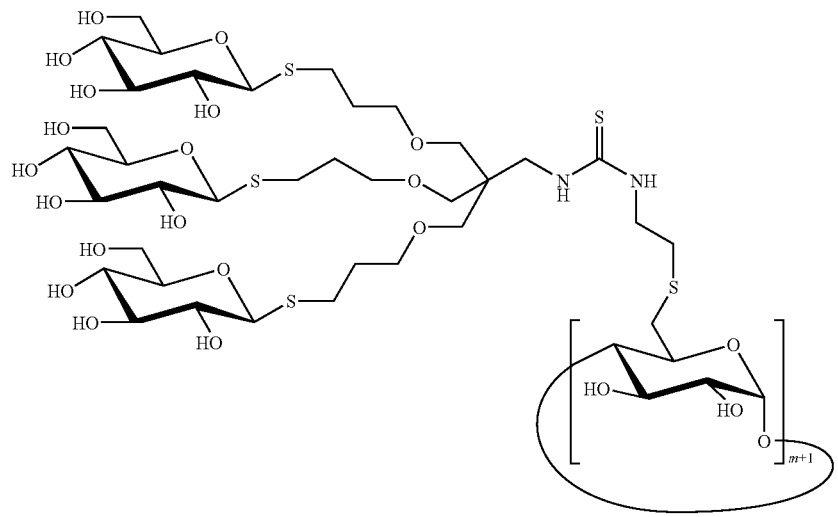
(V; R$_2$ = R$_3$ = β-D-glucopyranosyl)
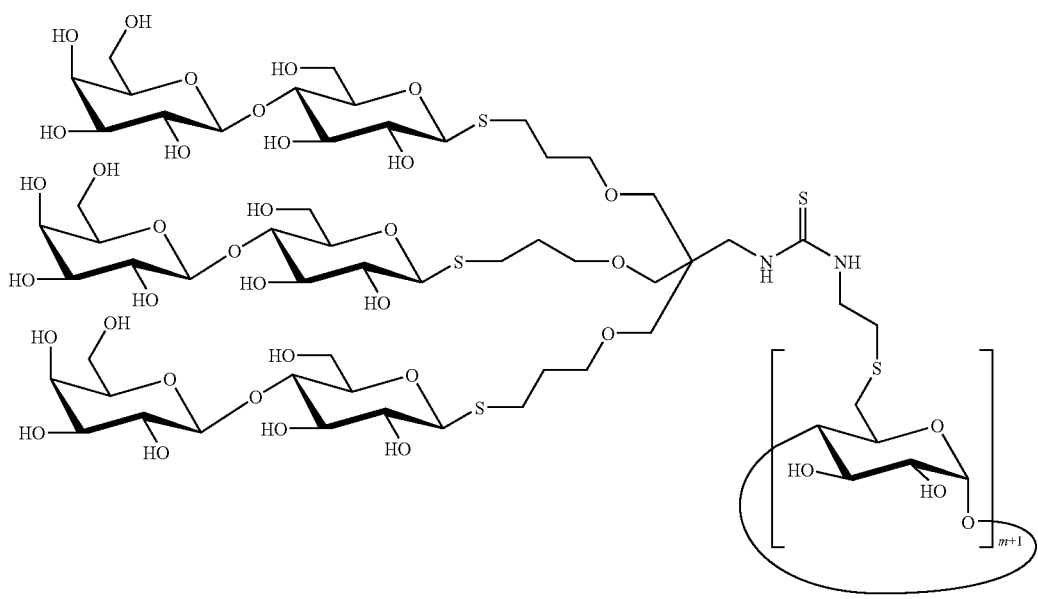
(V; R$_2$ = R$_3$ = β-lactosyl)

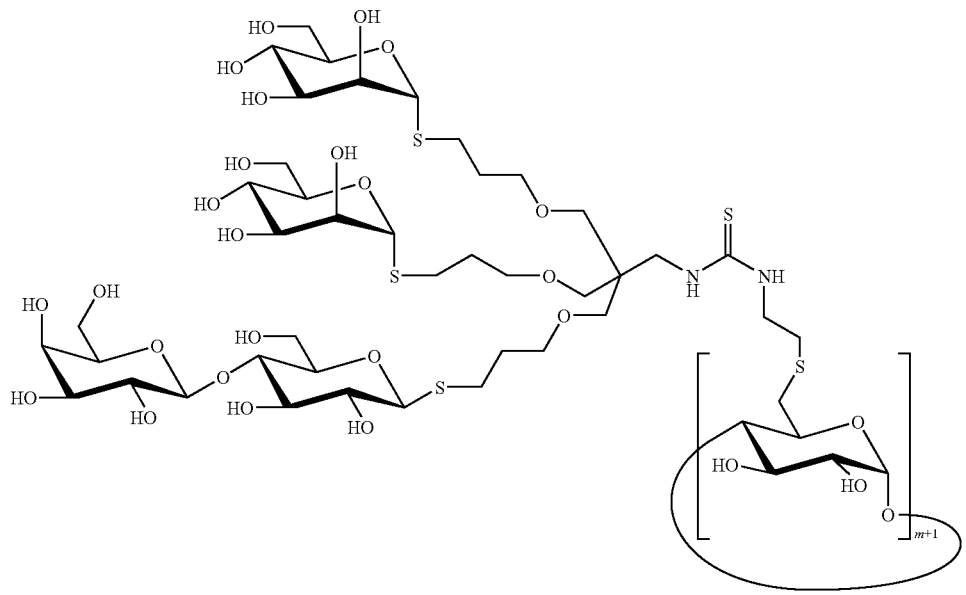
(V; R² = α-D-mannopyranosyl; R³ = β-lactosyl)
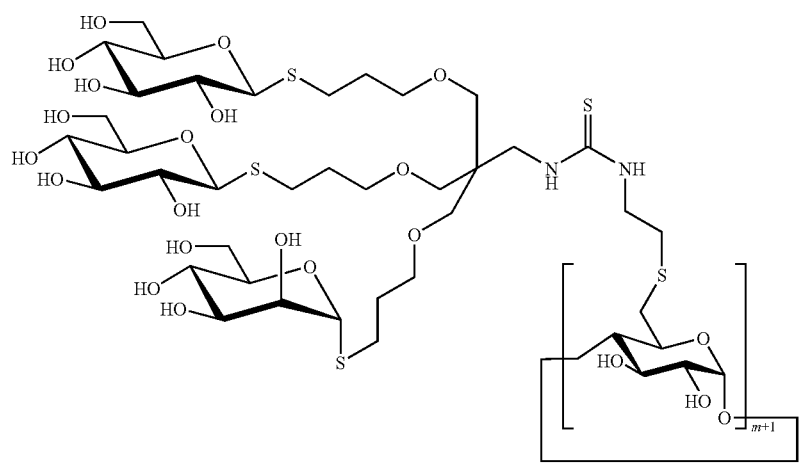
(V; R₂ = β-D-glucopyranosyl; R₃ = α-mannopyranosyl)

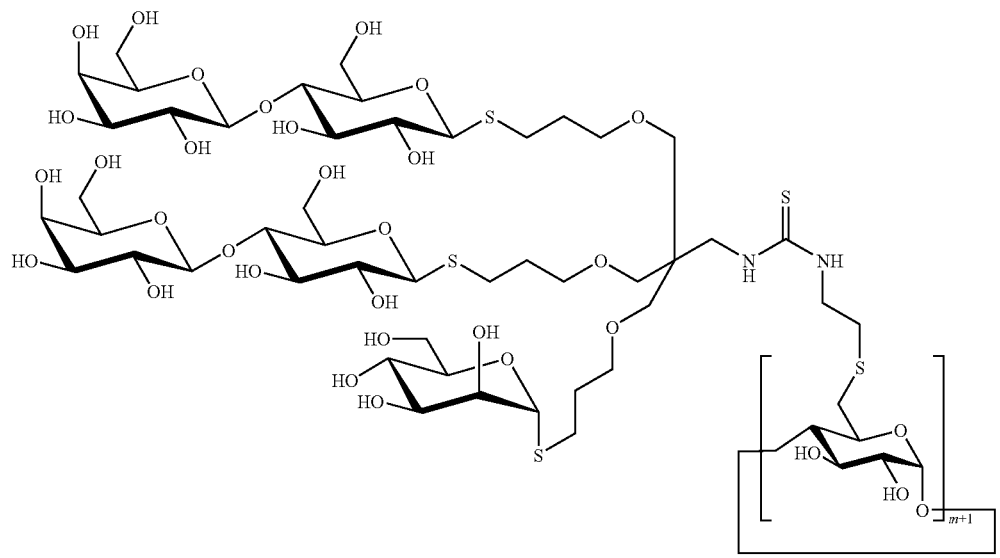
(V; R₂ = β-lactosyl; R₃ = α-D-mannopyranosyl)
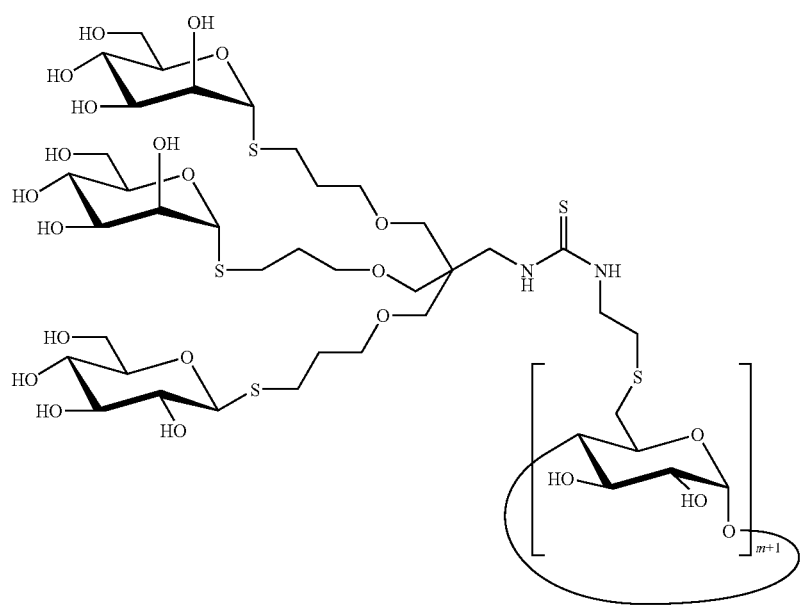
(V; R₂ = α-D-mannopyranosyl; R₃ = β-D-glucopyranosyl)

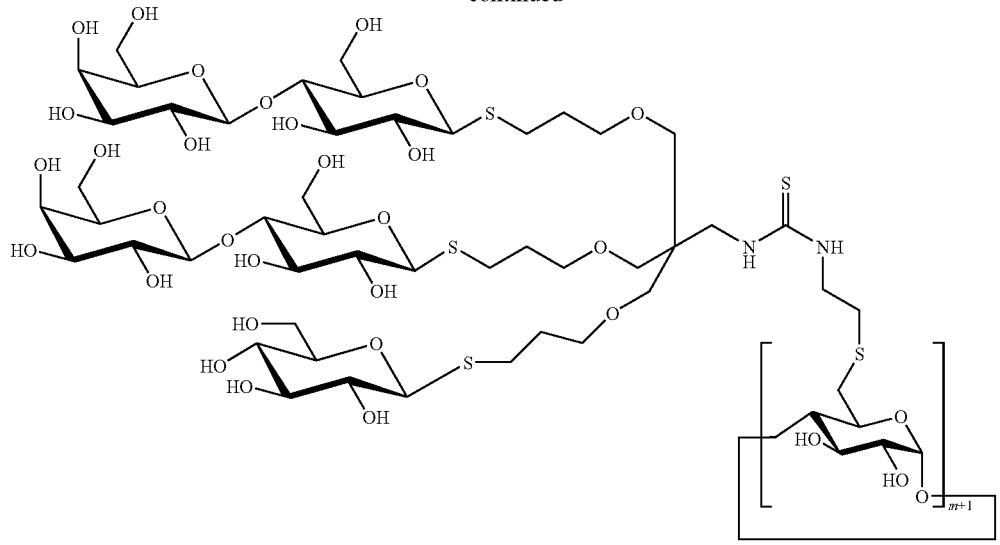

(V; $R_2$ = β-lactosyl; $R_3$ = β-D-glucopyranosyl)

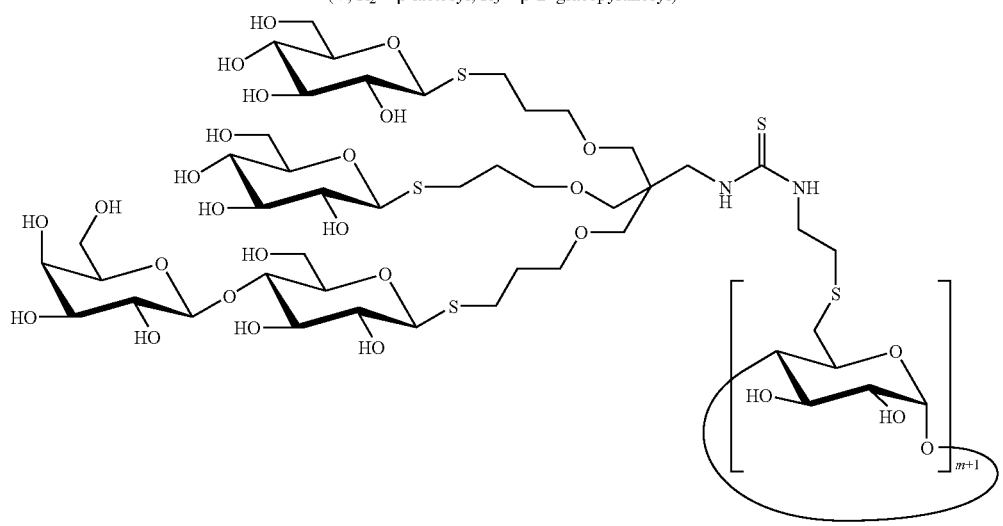

(V; $R_2$ = β-D-glucopyranosyl; $R_3$ = β-lactosyl)

The present invention also relates to a compound as defined above, characterized in that m is equal to 6.

The use of the cysteaminyl-cyclodextrins of the invention, corresponding to formula (I) where Z represents an amine group of the NHX type (X=H or alkyl substituent), as precursors for the preparation of derivatives per substituted in primary alcohol position by glucidic substituents presents advantages compared with other processes described previously. In particular, the formation of a thiourea bond has advantages from the point of view of the ease of operation, the yields and the purification of the final product which most often does not require chromatographic separation. Moreover, the presence of the spacer arm of the cysteaminyl type allows the steric hindrance to be reduced and allows the incorporation of a multiplication element in order to obtain hyperbranched derivatives which can be better recognized by specific cell receptors as a result of the multiplication of the recognition unit, which is not the case for the processes of the prior art, in particular for the international application WO 97/33919.

In fact, in the prior art, probably as a result of a steric hindrance, the per(6-amino-6-deoxy)cyclodextrins used as starting material in the preparation of the thioureido-cyclodextrins persubstituted in primary alcohol position and described in the document WO 97/33919, have a relatively poor nucleophilic reactivity, so that the reaction with isothiocyanates to create the thiourea bond only occurs correctly with activated isothiocyanates, such as glycosyl-isothiocyanates, which complicates the reaction and prevents the incorporation of multiplication elements. Moreover, the document *ChemBioChem* 2001 already cited shows that the resulting glycosylthioureido-cyclodextrins are poorly recognized by complementary specific lectins.

The present invention also relates to a process for the preparation of a compound as defined above, of formula (I), characterized in that it comprises the following stages:

the reaction of a compound selectively or totally halogenated in primary alcohol position, of the following formula (VII):

(VII)

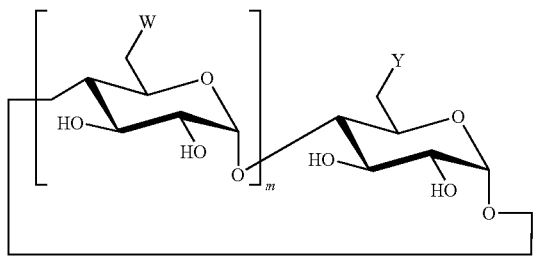

m being as defined above,

W representing an OH group or a Y group, the W groups all being identical, and Y representing a halogen atom chosen from the group constituted by chlorine, bromine, iodine, and preferably being bromine or iodine, with an ω-aminoalkanethiol of the following formula (VIII):

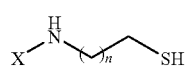
(VIII)

said ω-aminoalkanethiol optionally being N-alkylated, or the corresponding salt of the following formula (VIII-a):

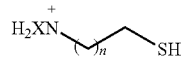
(VIII-a)

or a tetraalkylammonium salt of the following formula (VIII-b):

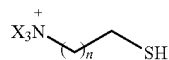
(VIII-b)

said salt being associated with a halide counter ion, preferably the chloride ion, n and X being as defined above, and X preferably being a hydrogen atom, the compound of formula (VIII) preferably being cysteamine of formula $H_2N-CH_2-CH_2-SH$, in order to obtain a compound as defined above and having the following formulae (A-a) or (A-b):

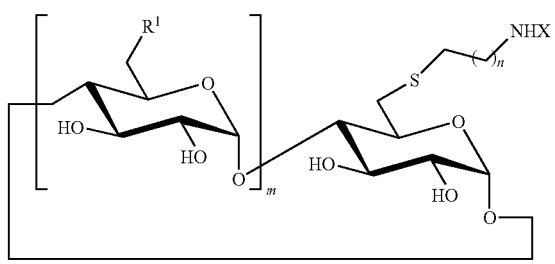
(A-a)

-continued

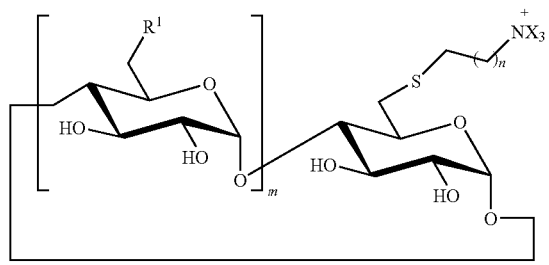
(A-b)

and optionally the reaction of the compound of formula (A-a) as obtained in the preceding stage with an isothiocyanate of the following formula (IX):

$$R-N=C=S \qquad (IX)$$

in which R is as defined above, in order to obtain a compound as defined above, and corresponding to the following formula:

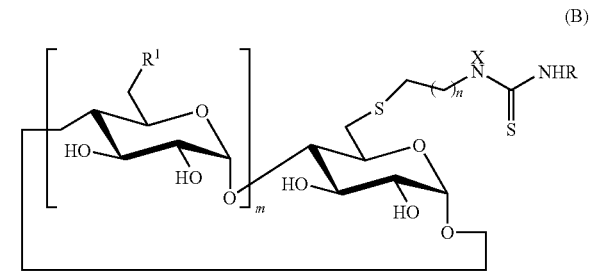
(B)

This process makes it possible to obtain compounds mono- and polysubstituted on the cyclodextrin ring.

The first stage of the process mentioned above is carried out in dimethylformamide in the presence of triethylamine (proportion of DMF/triethylamine of 4:1), and the mixture is stirred for 48 hours at ambient temperature. The yield of this stage is comprised between approximately 80 and 95%.

The second stage of this process is a coupling carried out in a water-acetone mixture (1:1 to 1:2) at pH 8-9 (sodium bicarbonate) at ambient temperature for 1 to 6 hours. The yield of this stage is comprised between approximately 55 and 95%.

The present invention also relates to a process for the preparation of a compound as defined above, corresponding to the following general formula (I-b):

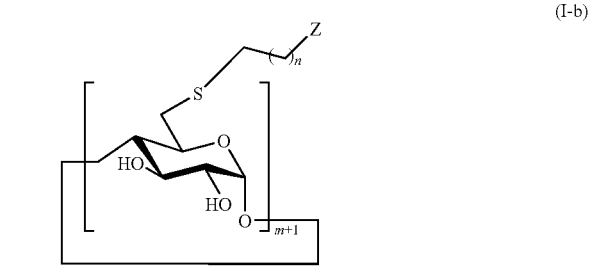
(I-b)

said process being characterized in that it comprises the following stages:

the reaction of a per(6-deoxy-6-halo) cyclodextrin compound, of the following formula (VII-a):

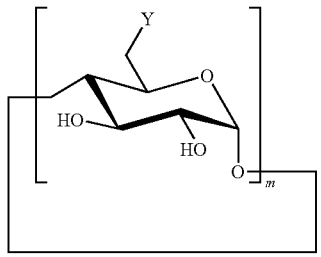
(VII-a)

m being as defined above, and Y representing a halogen atom chosen from the group constituted by chlorine, bromine, iodine, and preferably being bromine or iodine, with an ω-aminoalkanethiol of the following formula (VIII):

(VIII)

said ω-aminoalkanethiol optionally being N-alkylated,
or the corresponding salt of the following formula (VIII-a):

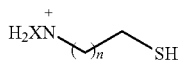
(VIII-a)

or a tetraalkylammonium salt of the following formula (VIII-b):

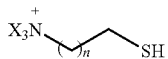
(VIII-b)

said salt being associated with a halide counter ion, preferably the chloride ion, n and X being as defined above, and X preferably being a hydrogen atom, the compound of formula (VIII) preferably being cysteamine of formula $H_2N-CH_2-CH_2-SH$, in order to obtain a compound of formula (I-c), (I-d) or (I-e), as defined above,

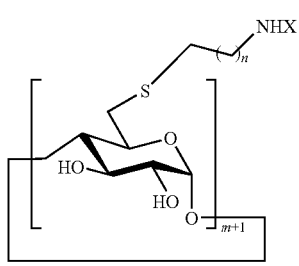
(I-c)

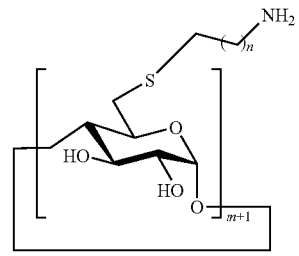
(I-d)

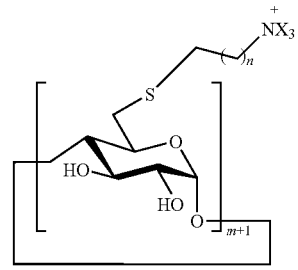
(I-e)

and optionally
the reaction of the compound of formula (I-c) as obtained in the preceding stage with an isothiocyanate of the following formula (IX):

$$R-N=C=S \qquad (IX)$$

in which R is as defined above,
in order to obtain a compound of formula (II) or (II-a), as defined above.

(II)

(II-a)

This process makes it possible to obtain compounds polysubstituted on the cyclodextrin ring.

The first stage of the process mentioned above is carried out in dimethylformamide in the presence of triethylamine (proportion of DMF/triethylamine of 4:1), and the mixture is stirred for 48 hours at ambient temperature. The yield of this stage is comprised between approximately 80 and 95%.

The second stage of this process is a coupling carried out in a water-acetone mixture (1:1 to 1:2) at pH 8-9 (sodium bicarbonate) at ambient temperature for 1 to 6 hours. The yield of this stage is comprised between approximately 55 and 90%.

The present invention also relates to a process for the preparation of a compound of formula (I-f-bis)

(I-f-bis)

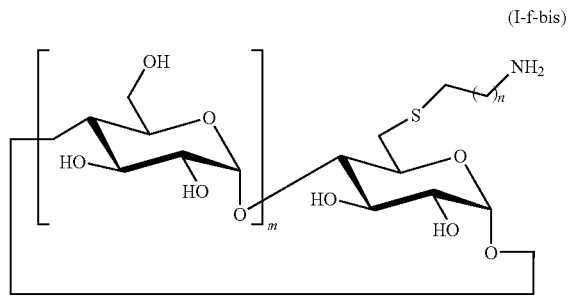

in which m and n are as defined above, n preferably being equal to 1, said process being characterized in that it comprises the reaction of a compound selectively halogenated in primary alcohol position, of the following formula (VII):

(VII)

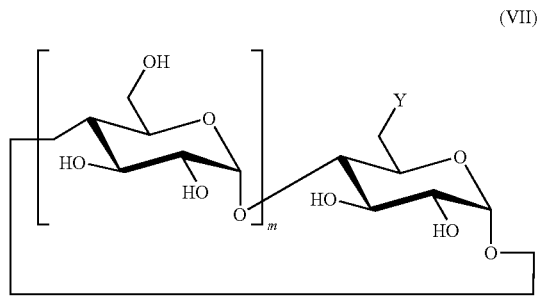

m being as defined above, and

Y representing a halogen atom chosen from the group constituted by chlorine, bromine, iodine, and preferably being bromine or iodine, with an ω-aminoalkanethiol of the following formula:

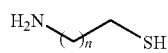

n being as defined above, or preferably with the cysteamine of formula $H_2N$—$CH_2$—$CH_2$—SH.

The present invention also relates to a process for the preparation of compounds as defined above, corresponding to the following formula:

(I-a)

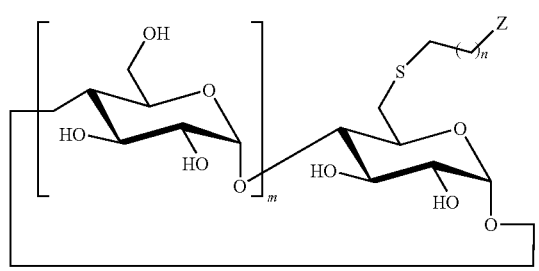

said process being characterized in that it comprises the following stages:

the reaction of a compound selectively halogenated in primary alcohol position, of the following formula (VII):

(VII)

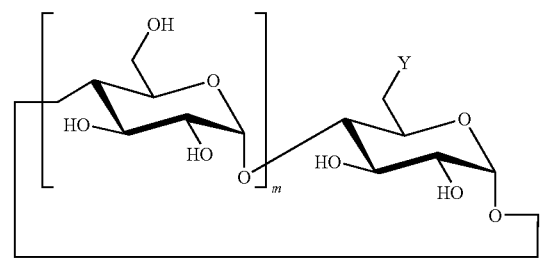

m being as defined above, and

Y representing a halogen atom chosen from the group constituted by chlorine, bromine, iodine, and preferably being bromine or iodine, with an ω-aminoalkanethiol of the following formula (VIII):

(VIII)

said ω-aminoalkanethiol optionally being N-alkylated, or the corresponding salt of the following formula (VIII-a):

(VIII-a)

or a tetraalkylammonium salt of the following formula (VIII-b):

(VIII-b)

said salt being associated with halide as a counter ion, and preferably being the chloride ion, n and X being as defined above, and X preferably being a hydrogen atom, the compound of formula (VIII) preferably being cysteamine of formula $H_2N$—$CH_2$—$CH_2$—SH, in order to obtain a compound of formula (I-f) or (I-g) as defined above, of the following formula:

(I-f)

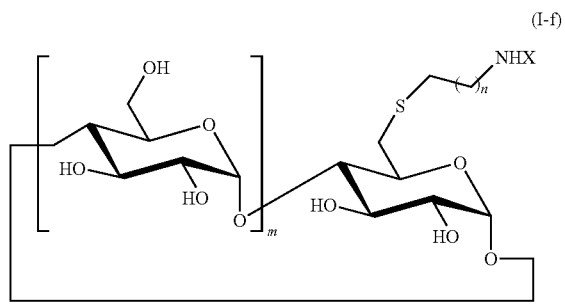

-continued (I-g)

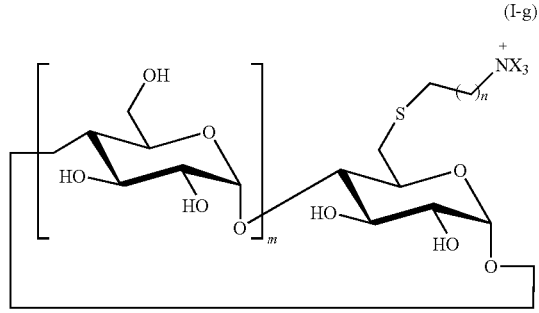

in which m, n and X are as defined above,
and optionally
the reaction of the compound of formula (I-f) as obtained in the preceding stage with an isothiocyanate of the following formula (IX):

R—N=C=S         (IX)

in which R is as defined above,
in order to obtain a compound as defined above, of formula (I-h):

(I-h)

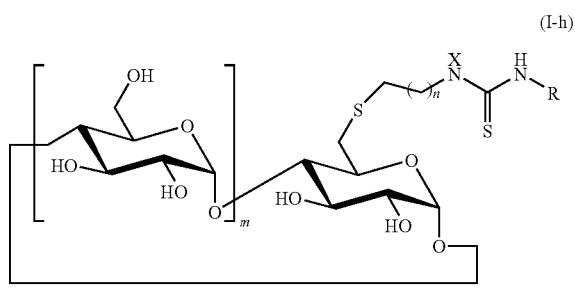

This process makes it possible to obtain the compounds monosubstituted on the cyclodextrin ring.

The first stage of the process mentioned above is carried out in dimethylformamide in the presence of triethylamine (proportion of DMF/triethylamine of 4:1), and the mixture is stirred for 48 hours at ambient temperature. The yield of this stage is comprised between approximately 85 and 95%.

The second stage of this process is a coupling carried out in a water-acetone mixture (1:1) at pH 8-9 (sodium bicarbonate) at ambient temperature for 1 to 3 hours. The yield of this stage is comprised between approximately 80 and 95%.

The derivatives of the invention of the cysteaminyl-cyclodextrin type of formula (I), in which the $R^1$ groups are all identical and represent S—$CH_2$—$(CH_2)_n$—Z, can be prepared by a process which consists of reacting a derivative of cyclodextrin persubstituted in primary alcohol position by halogenated groups, in particular per(6-bromo or 6-iodo-6-deoxy)cyclodextrins, with commercial cysteamine hydrochloride or, generally, with an ω-aminoalkanethiol halohydrate with 2 to 6 carbon atoms, optionally N-alkylated, in N,N-dimethylformamide in the presence of a base such as an amine such as triethylamine or N,N-dimethylaminopyridine, or a metal hydride such as sodium or lithium hydride. The derivatives of cyclodextrins persubstituted in primary alcohol position by halogenated groups, used as starting products in this process, can be prepared from commercial cyclodextrin in a single stage and with a good yield by reaction with various selective halogenation reagents. For this the processes described by J. Defaye et al. in the documents *Supramol. Chem*, 2000, 12, pp. 221-224, *Polish J. Chem.* 1999, 73, pp. 967-971, *Tetrahedron Lett.* 1997, 38, pp. 7365-7368, *Carbohydr. Res.* 1992, 228, pp. 307-314, and *Angew. Chem., Int. Ed. Engl.* 1991, 30, pp. 78-80 can be used.

The derivatives of the invention of the cysteaminyl-cyclodextrin type of formula (I) in which the $R^1$ groups are all identical and represent OH can be prepared by a process which consists of reacting a derivative of cyclodextrin monosubstituted in primary alcohol position by a halogenated group, in particular mono(6$^I$-bromo or 6$^I$-iodo-6$^I$-deoxy)cyclodextrins, with commercial cysteamine hydrochloride or, generally, with an ω-aminoalkanethiol halohydrate with 2 to 6 carbon atoms, optionally N-alkylated, according to the methodology described above for the preparation of the derivatives persubstituted in primary alcohol position. The derivatives of cyclodextrins monosubstituted in primary alcohol position by halogenated groups, used as starting products in this process, can be prepared from the 6$^I$-O-p-toluenesulphonyl cyclodextrin derivative in one stage and with a good yield by nucleophilic displacement of the tosylate group by a halide anion in N,N-dimethylformamide. For the preparation of the derivatives of cyclodextrins comprising a p-toluenesulphonate group on only one of the primary alcohol positions, the process described by J. Defaye et al. in the document WO 99/61483 or the methods described in the journal article by L. Jicsinszky et al. in *Comprehensive Supramolecular Chemistry*, Vol. 3 (Editors J. Szejtli and T. Osa), Pergamon, Oxford, 1996, pp. 57-198 can be used.

The invention also relates to derivatives of the cysteamninyl-cyclodextrin type of formula (I) in which the $R^1$ are different and represent OH or S—$CH_2$—$(CH_2)_n$—Z, with different substitution patterns. This type of derivative can be obtained starting with cyclodextrin derivatives selectively substituted by sulphonate type groups in primary alcohol position according to the sequence of reactions described above for the preparation of derivatives of the cysteaminyl-cyclodextrin type monosubstituted in primary alcohol position. For the preparation of the derivatives of cyclodextrin selectively polysubstituted in primary alcohol positions by groups of the sulphonate type, the processes described in the journal article by L. Jicsinszky et al. in *Comprehensive Supramolecular Chemistry*, Vol. 3 (Editors J. Szejtli and T. Osa), Pergamon, Oxford, 1996, pp. 57-198 can be used.

The process for the preparation of thioureidocysteaminyl-cyclodextrins of formula (II) of the invention consists of reacting a cysteaminyl-cyclodextrin of formula (I) where Z represents an amine group of the NHX type (X=H or alkyl substituent) with an isothiocyanate of formula R—NCS in which R has the meaning given above. This reaction can be carried out in an organic solvent such as pyridine or also in a mixture of water with a miscible organic solvent such as acetone.

When R is a group derived from a monosaccharide or an oligosaccharide, the isothiocyanate of formula R—NCS can be prepared by a reaction of the thiocarbonyl chloride on an aminodeoxyglycose or a glycosylamine. For this reaction the processes described by J. M. Garcia Fernandez and C. Ortiz Mellet in *Adv. Carbohydr. Chem. Biochem.* 1999, 55, pp. 35-135 can be followed.

When R comprises a branched multiplication element derived from tris(2-hydroxymethyl)methylamine (TRIS), the corresponding isothiocyanate can be prepared by a reaction of the thiocarbonyl chloride on the aminated derivative containing glucidic substituents on the primary alcohol positions, as described in the document *Chem. Commun.*, 2000, pp. 1489-1490. The aminated trivalent glycodendron precursor can be obtained by a glycosidation reaction of a TRIS derivative with the amine function suitably protected in the form of a carbobenzoxy derivative, as described by P. R. Ashton et al. in *J. Org. Chem.* 1998, 63, pp. 3429-3437.

When R comprises a branched multiplication element derived from pentaerythritol, the glycodendrons suitably functionalized with an isothiocyanate group can be prepared from commercial pentaerythritol by a sequence of reactions which involves:

(i) a selective triallylation by treatment with allyl bromide, which leaves a single hydroxyl group free;

(ii) the radical addition of a 1-thiosugar to the double bond of the allyl groups. This reaction can be carried out, either by activation with ultraviolet light, or in the presence of a free radical initiator such as azobis(isobutyronitrile) or p-nitroperbenzoic acid. By way of example, the reaction conditions described by D. A. Fulton and J. F. Stoddart in *Org. Lett.* 2000, 2, pp. 1113-1116 or by X.-B. Meng et al. in *Carbohydr. Res.* 2002, 337, pp. 977-981 can be adapted. We have discovered in particular that this reaction allows the sequential addition of the different glucidic branchings. It is thus possible to obtain homogeneous as well as heterogeneous glycodendrons in which the glucidic substituents correspond to the structures mentioned above. This approach also allows the incorporation of a substituent other than a glucidic derivative into the structure, in particular a probe of the fluorescent type such as a fluorescein derivative. The 1-thiosugar precursors can be prepared, either from corresponding glycosyl halides by reaction with thiourea followed by hydrolysis of the resulting isothiouronium salt, or from glycals by radical addition of thioacetic acid to the double bond. For these reactions the processes described in the journal articles published by J. Defaye and J. Gelas in *Studies in Natural Products Chemistry*, Vol. 8 (Editor Atta.ur Rahman), Elsevier, Amsterdam, 1991, pp. 315-357 and by H. Driguez in *Top. Curr. Chem.*, 1997, 187, pp. 85-116 can be followed;

(iii) the conversion of the remaining primary alcohol group into an isothiocyanate group. This conversion can be carried out for example by conversion of the hydroxyl group into a good leaving group such as p-toluenesulphonate or trifluoromethanesulphonate, followed by a nucleophilic displacement by the azide anion and isothiocyanation of the resulting azide by reaction with triphenylphosphine and carbon disulphide. For this conversion, the method described in the document *Chem. Commun.*, 2000, pp. 1489-1490 can be followed.

The processes described above for obtaining the cysteaminyl- and thioureido-cysteaminyl-cyclodextrins of the invention are very advantageous as they allow the obtention of the desired derivatives in a reduced number of stages and with high yields. Moreover, these processes make it possible to obtain hyperbranched homogeneous and heterogeneous derivatives which are not easily accessible by other means. These derivatives are very effectively recognized by specific membrane lectins, as a function of the incorporated glucidic substituents.

The present invention also relates to an inclusion complex of a compound as defined previously, with a pharmacologically active molecule, the molar ratio between the compound and the pharmacologically active molecule advantageously being approximately 50:1 to approximately 1:1.

The expression "inclusion complex" designates the supramolecular entity constituted by the compound according to the invention (host molecule) and the pharmacologically active molecule (guest molecule), in which the guest molecule is maintained in the hydrophobic cavity of the host molecule by means of non-covalent interactions.

The expression "pharmacologically active molecule" designates an active ingredient endowed with a therapeutic activity, such as an anticoagulant, antidiabetic, anti-inflammatory, antibiotic, antineoplastic agent etc.

The present invention also relates to a complex as defined above, characterized in that the pharmacologically active molecule is an antineoplastic agent, in particular belonging to the taxol family.

As antineoplastic agents there can be mentioned in particular, the non-biological antineoplastic agents approved by the FDA (Food and Drug Administration) such as:

alkylating agents: nitrosoureas such as: lomustine, carmustine and streptozocin; mustard oils such as: mechlorethamine, melphalan, uracil nitrogen mustard, chlorambucil, cyclophosphamide and iphosphamide; other alkylation agents such as: cisplatin, carboplatin, mitomycine, thiotepa, decarbazine, procarbazine, hexamethyl melamine, triethylenemelamine, bisulphan, pipobroman, and mitotane;

antimetabolites: methotrexate, trimetrexate, pentostatin, cytarabine, ara-CMP, fludarabine phosphate, hydroxyurea, fluorouracil, floxuridine, chlorodeoxyadenosine, gemcitabine, thioguanine and 6-mercaptopurine;

DNA cleaving agents: bleomycin; topoisomerase I poisons such as: topotecan, irinotecan, camptothecin sodium salt and analogues of topotecan and irinotecan; topoisomerase II poisons such as: daunorubicin, doxorubicin, idarubicin, mitoxantrone, teniposide and etoposide;

DNA intercalation agents: dactinomycin and mithramycin;

mitosis inhibitors: vinblastine, vincristine, navelbine, paclitaxel and docetaxel.

A preferred antineoplastic agent, belonging to the taxol family, is docetaxel (Taxotere®).

The affinity of the thioureidocysteaminyl-cyclodextrins of the invention for specific membrane lectins was evaluated in vitro following the ELLA (Enzyme-Linked Lectin Assay) protocol. Numerous examples of application of this protocol can be found in the journal article of J. J. Lundquist and E. J. Toon in *Chem. Rev.* 2002, 102, pp. 555-578. This technique measures the capacity of a soluble mono- or oligosaccharide ligand to inhibit the association between a complementary lectin and another reference ligand fixed to a plastic support microplate. Thus, the thioureidocysteaminyl-cyclodextrins carrying α-D-mannopyranosyl substituents are recognized by concanavalin A or by the lectin specific to the mannose of the macrophages, the derivatives with β-lactosyl substituents are recognized by the lectin specific to *Arachys hypogaea* lactose or to hepatocytes, and the derivatives comprising the sialyl-Lewis X tetrasaccharide substituent are recognized by the endothelium selectins involved in the inflammation process.

In general, a substantial increase in the affinity of the thioureidocysteaminyl-cyclodextrin type derivatives for the specific lectins is observed compared with the thioureido-cyclodextrin-type conjugates described in the document *ChemBioChem* 2001.

The thioureidocysteaminyl-cyclodextrins of the invention comprising cell recognition elements can in particular be used to mask complementary membrane receptors. Thus, it is possible to block the receptor specific to the mannose of the macrophages by means of the polymannosylated thioureidocysteaminyl-cyclodextrins, the receptor specific to lactose of the hepatic cells by means of the polylactosylated derivatives and the endothelium selectins by means of derivatives incorporating substituents derived from sialyl Lewis X tetrasaccharide. In this context, these derivatives can be used as active molecules for the prevention and the treatment of the infection and cancerization processes involving adhesion phenomena and, also, for the prevention and the treatment of the diseases linked with disturbance of the inflammation process.

These inclusion compounds can be prepared by standard processes, for example by dispersion of the active molecule in solution or in the pure state in a solution of the cyclodextrin derivative, in the presence or not in the presence of a cosolvent, as described in the document WO 97/33919.

These inclusion complexes can be prepared for example by adding to a solution or a suspension of the compound of the invention of formula (I) the pharmacologically active molecule in solution or in the pure state. The inclusion complex thus formed can be isolated by freeze-drying.

In the case where the pharmacologically active molecule is added in solution, for example an antineoplastic agent of the taxol family, a concentrated solution of the molecule in an organic solvent miscible with water, for example acetone, is used and the mixture obtained is subjected to stirring and to bubbling through of inert gas such as nitrogen, in order to eliminate the organic solvent.

In the case of the compounds of the taxol family, such as Taxotere®, it is also possible to disperse this product in the pure state in a sterile solution of a compound according to the invention.

The present invention also relates to a pharmaceutical composition comprising a compound as defined above, or an inclusion complex as defined above, with a pharmacologically acceptable vehicle.

The present invention also relates to a pharmaceutical composition as defined above, in the form of an aqueous solution.

The present invention also relates to a pharmaceutical composition as defined above, characterized in that it contains per single dose approximately 50 mg to approximately 500 mg of one of the compounds as defined previously, or in that it contains per single dose approximately 100 mg to approximately 750 mg of one of the complexes as defined above.

These pharmaceutical compositions, which can be administered by oral or parenteral route, are for example solutions, powders, suspensions, etc., in particular injectable solutions.

KEY TO THE FIGURES

FIG. 1 represents the variation in the inhibition of the association between the ConA lectin and the yeast mannan in the presence of compounds No. 2, No. 3, No. 4, No. 6 and No. 7, as well as for heptakis(6-deoxy-6-α-D-mannopyranosylthioureido)cyclomalto-heptaose (derived from per-(C-6)-amine β-cyclodextrin), as a function of the ligand concentration in μM.

The solid line curve with the black circles corresponds to the heptavalent derivative of per-(C-6)-amine β-cyclodextrin; the dotted line curve with the crosses corresponds to compound No. 2; the solid line curve with the crosses corresponds to compound No. 3; the solid line curve with the white triangles corresponds to compound No. 4; the solid line curve with the white diamonds corresponds to compound No. 6 and the dotted line curve with the black squares corresponds to compound No. 7.

EXPERIMENTAL PART

Example 1

Preparation of heptakis[6-S-(2-aminoethyl-6-thio)] cyclomaltoheptaose heptahydrochloride (compound No. 1)

This compound corresponds to formula (I) given above with n=1, m=6, in which all the $R^1$s are identical and represent S—$CH_2$—$(CH_2)_n$—Z, Z representing an $NH_2$ group, and was isolated in the form of its heptahydrochloride.

Triethylamine (2.5 mL) is added to a solution of 2-aminoethanethiol hydrochloride (999 mg, 8.8 mmol) in distilled DMF (10 mL), under argon, using a syringe. It is observed that the suspension becomes violet. A solution of heptakis[6-bromo-6-deoxy]cyclomaltoheptaose (1 g) in DMF (5 mL) is added dropwise to this suspension. The reaction mixture is stirred for 48 hours at ambient temperature. The appearance of a white precipitate is then observed. The solid is filtered and solubilized in water (20 mL), the pH of the solution is adjusted to 4 by addition of diluted hydrochloric acid and finally the solution is freeze-dried. The solid residue is placed in suspension in 96% ethanol and the suspension is stirred for 30 minutes, then filtered and dried. Compound No. 1 (976 mg, 86%) is thus obtained with the following characteristics:

$[\alpha]_D$+81.40° (c 1.0; water)

mass spectrum (electrospray): m/z 1549 (100%, [M+Na]$^+$)

solubility in water: 500 g.L$^{-1}$ (323 mmol.L$^{-1}$)

$^1$H NMR data (500 MHz, $D_2O$): δ 5.03 (7H, d, $J_{1,2}$ 3.5 Hz, H-1), 3.93 (7H, td, $J_{4,5}$ 9.2 Hz, $J_{5,6b}$ 7.0 Hz, $J_{5,6a}$ 2.0 Hz, H-5), 3.82 (7H, t, $J_{2,3}$=$J_{3,5}$ 9.4 Hz, H-3), 3.56 (7H, dd, H-2), 3.55 (7H, t, H-4), 3.17 (14H, t, $^3J_{H,H}$ 6.8 Hz, $CH_2N$), 3.08 (7H, dd, $J_{6a,6b}$ 13.5 Hz, H-6a), 2.91 (14H, t, $^3J_{H,H}$ 6.8 Hz, $CH_2S$), 2.90 (7H, dd, H-6b)

$^{13}$C NMR data (125.7 MHz, $D_2O$): δ 101.6 (C-1); 83.6 (C-4); 72.7 (C-3); 72.0 (C-2); 71.6 (C-5); 38.6 ($CH_2N$); 32.7 (C-6); 30.0 ($CH_2S$).

Example 2

Preparation of heptakis[6-S-[2-[N'-(α-D-mannopyranosyl)thioureido]ethyl-6-thio]cyclomaltoheptaose (compound No. 2)

This compound corresponds to formula (II) given above with n=1, m=6, X representing a hydrogen atom and R corresponding to the formula:

(III)

This compound is obtained by condensation of compound No. 1 (see example 1) with 2,3,4,6-tetra-O-acetyl-α-D-mannopyranosyl isothiocyanate followed by an alkaline hydrolysis of the acetyl protective group.

Solid sodium hydrogen carbonate is added to a solution of compound No. 1 (25 mg, 14 μmol) in water (2 mL) until the pH reaches values of between 8 and 9. After 20 minutes, a 2,3,4,6-tetra-O-acetyl-α-D-mannopyranosyl isothiocyanate solution (42 mg, 0.11 mmol, 1.1 equiv.) in acetone (3 mL) is added and the reaction mixture is stirred at ambient temperature for 1 hour. The acetone is evaporated in the rotary evaporator and the resulting aqueous solution is freeze-dried. The residue is taken up by methanol, filtered and concentrated. The resulting solid is dissolved in methanol (6 mL), to which a 1 N solution of sodium methylate in methanol (196 μL, 0.5 equiv.) is added and the solution is stirred at 0° C. for 5 minutes. The precipitation of a white solid which is redissolved in water (8 mL) is observed. The aqueous solution is stirred at 0° C. for 15 minutes, neutralized and demineralized by successive treatment with Amberlite IR-120 (H$^+$) ion exchange resin and Duolite MB-6331 (H⁺, OH⁻) mixed resin, filtered and freeze-dried. After purification by gel-filtration chromatography (Sephadex G-25), compound No. 2 is obtained (30 mg, 71%) with the following characteristics:

$[\alpha]_D$ +50.30° (c 1.0, water)

mass spectrum (MALDITOF): m/z 3103.9 [M+H]⁺ solubility in water: 780 g.L⁻¹ (251 mmol.L⁻¹)

¹H NMR data (500 MHz, 333 K, D₂O): δ 5.85 (7H, bs, H-1'); 5.43 (7H, bs, H-1); 4.34 (7H, m, H-2'); 4.30 (7H, m, H-6a'); 4.28 (7H, m, H-5); 4.22 (7H, m, H-3); 4.15 (7H, d, $J_{6a',6b'}$ 12.0 Hz, H-6b'); 4.01 (7H, m, H-3'); 3.96 (7H, m, H-2); 3.92 (7H, t, $J_{3',4'}=J_{4',5'}$ 9.0 Hz, H-4'); 3.88 (7H, m, H-4); 3.80 (14H, m, CH₂S); 3.75 (7H, m, H-5'); 3.72 (14H, m, CH₂N); 3.55 (7H, m, H-6a); 3.53 (7H, m, H-6b)

¹³C NMR data (125.7 MHz, 333 K, D₂O): δ 181.7 (CS); 101.7 (C-1); 82.5 (C-1'); 84.1 (C-4); 73.5 (C-5'); 73.0 (C-3); 72.0 (C-2, C-5); 70.5 (C-3'); 69.5 (C-2'); 66.6 (C-4'); 60.7 (C-6'); 44.2 (CH₂N); 33.2 (C-6); 31.6 (CH₂S).

Example 3

Preparation of heptakis[6-S-[2-N'-tris(α-D-mannopyranosyloxymethyl)methylthioureido]ethyl-6-thio]cyclomaltoheptaose (compound No. 3)

This compound corresponds to formula (II) given above with n=1, m=6, X representing a hydrogen atom and R corresponding to the formula:

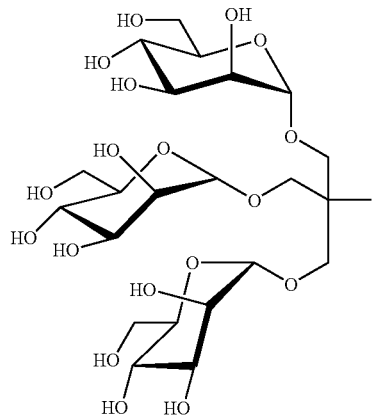

(IV)

This compound is obtained by condensation of compound No. 1 (see example 1) with tris(2,3,4,6-tetra-O-acetyl-α-D-mannopyranosyloxymethyl)methyl isothiocyanate followed by an alkaline hydrolysis of the acetyl protective group.

Solid sodium hydrogen carbonate is added to a solution of compound No. 1 (10 mg, 5.5 μmol), in water (1 mL) until the pH reaches values of between 8 and 9. After 20 minutes, a solution of tris(2,3,4,6-tetra-O-acetyl-α-D-mannopyranosyloxymethyl)methyl isothiocyanate (45 mg; 40 μmol; 1.04 equiv.) in acetone (1 mL) is added and the reaction mixture is stirred at ambient temperature for 4 hours. The acetone is evaporated in the rotary evaporator and the resulting aqueous solution is extracted with dichloromethane (3×5 mL). The organic solvent is evaporated, the residue is dissolved in methanol (3 mL) and a 1 N solution of sodium methylate in methanol is added up to pH 8-9 and the solution is stirred at ambient temperature for 5 minutes. The precipitation of a white solid which is redissolved by addition of water 1 mL) is observed. The aqueous solution is stirred at ambient temperature for 15 minutes, neutralized and demineralized by successive treatment with Amberlite IR-120 (H⁺) ion exchange resin and Duolite MB-6331 (H⁺, OH⁻) mixed resin, filtered and freeze-dried. After purification by gel-filtration chromatography (Sephadex G-25) compound No. 3 is obtained (15 mg, 45%) with the following characteristics:

$[\alpha]_D$ 130.0° (c, 0.5, water)

mass spectrum (MALDITOF); m/z 6108.53 ([M+H]⁺)

solubility in water: 800 g.L⁻¹ (131 mmol.L⁻¹)

¹H NMR data (500 MHz, 343 K, D₂O): δ 5.53 (7H, bs, H-1); 5.31 (21H, s, H-1'); 4.49 (21H, d, $^2J_{H,H}$ 10.5 Hz, OCH₂a); 4.41 (3H, s, H-2'); 4.40 (7H, m, H-5); 4.36 (21H, d, OCH₂b); 4.32 (7H, m, H-3); 4.29 (21H, d, $J_{6a',6b'}$ 12.0 Hz, H-6a'); 4.21 (14H, m, CH₂N); 4.20 (21H, dd, $J_{2',3'}$ 4.0 Hz, $J_{3',4'}$ 10.0 Hz, H-3'); 4.18 (21H, m, H-6b'); 4.12 (21H, t, $J_{4',5'}$ 10.0 Hz, H-4'); 4.09 (7H, m, H-2); 4.02 (7H, m, H-5'); 3.78 (7H, m, H-4); 3.26 (7H, m, H-6a); 3.47 (7H, m, $J_{5,6b}$ 8.5 Hz, H-6b); 3.22 (2H, m, CH₂S).

¹³C NMR data (125.7 MHz, 323 K, D₂O): δ 181.0 (CS); 102.6 (C-1); 100.9 (C-1'); 84.3 (C-4); 73.7 (C-5'); 73.5 (C-3); 72.6 (C-2, C-5); 71.3 (C-3'); 70.5 (C-2'); 6.73 (C-4', OCH₂); 61.4 (C-6'); 44.8 ($C_q$, CH₂N); 34.2 (C-6); 32.8 (CH₂S).

The examples which follow relate to hyperbranched thioureidocysteaminyl-cyclodextrins which comprise a multiplication element derived from pentaerythritol corresponding to the following formula:

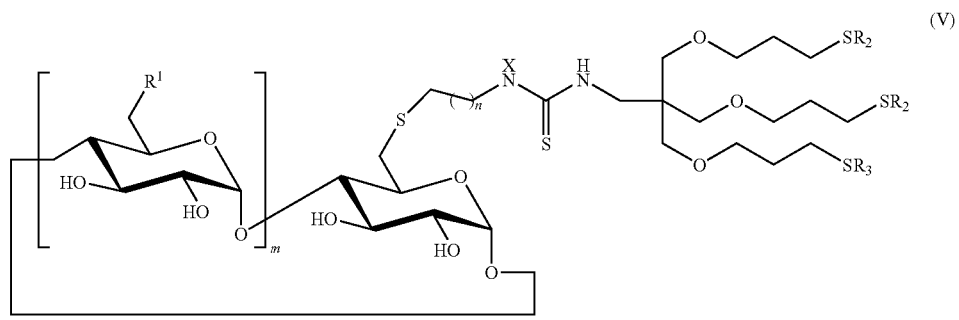

(V)

The universal precursor of the glycodendrons used in the synthesis of these derivatives is 2,2,2-tris(2-oxapent-4-enyl)ethanol (tri-O-allylpentaerythritol), obtained from commercial pentaerythritol.

A suspension of pentaerythritol (1.36 g, 10 mmol) in aqueous 40% sodium hydroxide is stirred vigorously at 70-75° C. for 15 minutes. Allyl bromide (3.2 mL, 40 mmol, 4 equiv.) is added dropwise and stirring is continued for 1 hour. The reaction mixture is extracted with dichloromethane (3×20 mL) and the organic phase is washed with water, dried (anhydrous sodium sulphate) and concentrated. The residue is purified by silica gel column chromatography with ethyl acetate-petroleum ether 1:4. Thus 1.28 g (yield 50%) of a colourless oil is obtained, having the following characteristics:

mass spectrum (FAB$^+$): m/z 257 (100%, [M+H]$^+$)

Example 4

Preparation of heptakis[6-S-[2-N'-[2,2,2-tris[5-(1-thio-α-D-mannopyranosyl)-2-oxapentyl]ethyl]thioureido]ethyl-6-thio]cyclomaltoheptaose
(compound No. 4)

This compound corresponds to formula (V) given above with n=1, m=6, in which all the R$^1$s are identical and represent CH$_2$—C[(CH$_2$OCH$_2$CH$_2$CH$_2$R$_2$)$_2$(CH$_2$OCH$_2$CH$_2$CH$_2$R$_3$)], X represents a hydrogen atom, R$_2$ and R$_3$ correspond to formula III (see example No. 2).

This compound is obtained by condensation of compound No. 1 (see example 1) with 2,2,2-tris[5-(2,3,4,6-tetra-O-acetyl-1-thio-α-D-mannopyranosyl)-2-oxapentyl]ethyl isothiocyanate followed by an alkaline hydrolysis of the acetyl protective group.

1. Preparation of 2,2,2-tris[5-(2,3,4,6-tetra-O-acetyl-1-thio-α-D-mannopyranosyl)-2-oxapentyl]ethyl isothiocyanate This compound is prepared by carrying out the following stages:

a) Preparation of 2,2,2-tris[5-(2,3,4,6-tetra-O-acetyl-1-thio-α-D-mannopyranosyl)-2-oxapentyl]ethanol A solution of tri-O-allylpentaerythritol (0.32 g; 1.3 mmol) and 2,3,4,6-tetra-O-acetyl-1-thio-α-D-mannopyranose (2.12 g; 5.85 mmol; 1.5 equiv.) in gas-free anhydrous methanol and under argon is irradiated with ultraviolet light at ambient temperature for 6 hours. The solvent is evaporated and the residue is purified by silica gel column chromatography with ethyl acetate-petroleum ether 1:2. Thus 0.81 g (yield 46%) of a white solid is obtained, having the following characteristics:

[α]$_D$+84.6° (c 1.0; dichloromethane)
mass spectrum (FAB$^+$): m/z 1371 (100%, [M+Na]$^+$)

b) Preparation of 2,2,2-tris[5-(2,3,4,6-tetra-O-acetyl-1-thio-α-D-mannopyranosyl)-2-oxapentyl]ethyl azide Pyridine (402 μL) and trifluoromethanesulphonic anhydride (177 μL) are added to a solution of 2,2,2-tris[5-(2,3,4,6-tetra-O-acetyl-1-thio-α-D-mannopyranosyl)-2-oxapentyl]ethanol (1.15 g; 0.85 mmol) in dichloromethane (5.5 mL). The reaction mixture is stirred for 20 minutes at −25° C., washed with a cold saturated solution of sodium hydrogen carbonate, dried with anhydrous magnesium sulphate and concentrated. The residue is taken up with N,N-dimethylformamide and sodium azide (166 mg; 2.55 mmol; 3 equiv.) is added. The suspension is stirred at ambient temperature for 3 hours and concentrated. The residue is taken up with dichloromethane, washed with water, dried with anhydrous magnesium sulphate, concentrated and purified by silica gel column chromatography with ethyl acetate-petroleum ether 1:2. Thus 1.0 g of a white solid (yield 86%) is obtained having the following characteristics:

[α]$_D$+83.20° (c 0.7; dichloromethane)
mass spectrum (FAB$^+$): m/z 1396 (100%, [M+Na]$^+$)

c) Preparation of 2,2,2-tris[5-(2,3,4,6-tetra-O-acetyl-1-thio-α-D-mannopyranosyl)-2-oxapentyl]ethyl isothiocyanate Triphenylphosphine (32 mg; 0.12 mmol; 1.1 equiv.) and carbon disulphide (0.1 mL; 1.1 mmol, 10 equiv.) are added to a solution of 2,2,2-tris[5-(2,3,4,6-tetra-O-acetyl-1-thio-α-D-mannopyranosyl)-2-oxapentyl]ethyl azide (0.15 g; 0.11 mmol) in dioxane (10 mL), and the reaction mixture is stirred at ambient temperature for 24 hours. The solvent is then evaporated and the residue is purified by silica gel column chromatography with ethyl acetate-petroleum ether 1:1. Thus 0.13 g (yield 85%) of a white solid is obtained having the following characteristics:

[α]$_D$+61.90° (c 0.4; dichloromethane)
mass spectrum (FAB$^+$): m/z 1412 (100%, [M+Na]$^+$)

2. Preparation of Compound No. 4

This compound is obtained by condensation of compound No. 1 (20 mg, 11.1 μmol) with 2,2,2-tris[5-(2,3,4,6-tetra-O-acetyl-1-thio-α-D-mannopyranosyl)-2-oxapentyl]ethyl isothiocyanate (160 mg, 115 μmol, 1.5 equiv.) in water-acetone (1:2, 3 mL) at pH 8-9 (solid sodium hydrogen carbonate) as described above for the preparation of compound No. 3. The reaction mixture is stirred for 48 hours at ambient temperature, the acetone is evaporated and the aqueous phase is extracted with ethyl acetate (3×5 mL). The organic phase is then dried with anhydrous magnesium sulphate and concentrated. The residue is purified by silica gel column chromatography with an acetonitrile-water gradient of 20:1 to 10:1. The resulting product is deacetylated and demineralized as described above for the preparation of compound No. 3. After freeze-drying, compound No. 4 is obtained (50 mg, 60%) having the following characteristics:

[α]$_D$+104.00° (c 1.0; water)
mass spectrum (MALDITOF): m/z 7751.88 ([M+H]$^+$)
solubility in water: 800 g.L$^{-1}$ (103 mmol.L$^{-1}$)

$^1$H NMR data (500 MHz, 353 K, D$_2$O): δ 5.82 (21H, s, H-1'); 5.61 (7H, bs, H-1); 4.57 (21H, m, H-2'); 4.46 (7H, m, H-5); 4.43 (28H, m, H-3, H-5'); 4.36 (63H, m, H-3', H-6", H-6b'); 4.29 (21H, m, H-4'); 4.23 (14H, m, CH$_2$N$_{cyst}$); 4.19 (7H, m, H-2); 4.09 (49H, m, H-4, H-3$_{Pent}$); 3.96 (56H, m, CH$_2$N$_{branch}$, H-1$_{Pent}$); 3.82 (7H, m, H-6a); 3.50 (7H, m, H-6b); 3.47 (14H, m, CH$_2$S$_{cyst}$); 3.26 (42H, bt, J$_{5a, 5b}$ 11.5 Hz, H-5$_{Pent}$); 2.46 (42H, m, H-4$_{Pent}$)

$^{13}$C NMR data (125.7 MHz, 343 K, D$_2$O): δ 181.9 (CS); 102.7 (C-1); 85.3 (C-1'); 85.1 (C-4); 73.9 (C-5'); 73.4 (C-3); 72.9 (C-2, C-5); 72.6 (C-2'); 72.1 (C-3); 7.11 (C-1$_{Pent}$); 70.9 (C-3$_{Pent}$); 67.7 (C-4'); 61.6 (C-6'); 46.6 (CH$_2$N$_{cyst}$, CH$_2$N$_{branch}$); 45.0 (C$_q$); 34.1 (C-6); 33.2 (CH$_2$S$_{cyst}$); 29.8 (C-4$_{Pent}$); 28.5 (C-5$_{Pent}$)

Example 5

Preparation of heptakis[6-S-[2-N'-[2,2,2-tris[5-(1-thio-β-D-glucopyranosyl)-2-oxapentyl]ethyl]thioureido]ethyl-6-thio]cyclomaltoheptaose
(compound No. 5)

This compound corresponds to formula (V) given above with n=1, m=6, in which all the $R^1$s are identical and represent $CH_2$—$C[(CH_2OCH_2CH_2CH_2R_2)_2(CH_2OCH_2CH_2CH_2R_2)]$, X represents a hydrogen atom, $R_2$ and $R_3$ correspond to the formula:

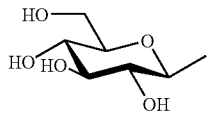
(VI)

This compound is obtained by condensation of compound No. 1 (see Example 1) with 2,2,2-tris[5-(2,3,4,6-tetra-O-acetyl-1-thio-β-D-glucopyranosyl)-2-oxapentyl]ethyl isothiocyanate followed by an alkaline hydrolysis of the protective acetyl group.

1. Preparation of 2,2,2-tris[5-(2,3,4,6-tetra-O-acetyl-1-thio-α-D-mannopyranosyl)-2-oxapentyl]ethyl isothiocyanate This compound is prepared with the following stages:

a) Preparation of 2,2,2-tris[5-(2,3,4,6-tetra-O-acetyl-1-thio-β-D-glucopyranosyl)-2-oxapentyl]ethanol This compound is obtained from tri-O-allylpentaerythritol (0.32 g; 1.3 mmol) and 2,3,4,6-tetra-O-acetyl-1-thio-β-D-glucopyranose (2.12 g; 5.85 mmol; 1.5 equiv.) by irradiation with ultraviolet light (250 nm) as described above for the preparation of 2,2,2-tris [5-(2,3,4,6-tetra-O-acetyl-1-thio-α-D-mannopyranosyl)-2-oxapentyl]ethanol. Thus 1.23 g (yield 70%) of a white solid is obtained, having the following characteristics:

$[\alpha]_D$–22.8° (c 0.8; dichloromethane)
mass spectrum (FAB$^+$): m/z 1371 (100%, [M+Na]$^+$)

b) Preparation of 2,2,2-tris[5-(2,3,4,6-tetra-O-acetyl-1-thio-β-D-glucopyranosyl)-2-oxapentyl]ethyl azide This compound is obtained from 2,2,2-tris[5-(2,3,4,6-tetra-O-acetyl-1-thio-β-D-glucopyranosyl)-2-oxapentyl] ethanol (1.15 g; 0.85 mmol) by reaction with trifluoromethanesulphonic anhydride followed by treatment with sodium azide as described above for the preparation of 2,2,2-tris[5-(2,3,4,6-tetra-O-acetyl-1-thio-α-D-mannopyranosyl)-2-oxapentyl]ethyl azide. Thus 0.73 g of a white solid is obtained (yield 60%) having the following characteristics:

$[\alpha]_D$+78° (c 0.9; dichloromethane)
mass spectrum (FAB$^+$): m/z 1396 (100%, [M+Na]$^+$)

c) Preparation of 2,2,2-tris[5-(2,3,4,6-tetra-O-acetyl-1-thio-β-D-gluopyranosyl)-2-oxapentyl]ethyl isothiocyanate This compound is obtained by isothiocyanation of 2,2,2-tris[5-(2,3,4,6-tetra-O-acetyl-1-thio-β-D-glucopyranosyl)-2-oxapentyl]ethyl azide (0.32 g; 0.23 mmol) by treatment with triphenylphosphine (67.1 mg; 0.26 mmol; 1.1 equiv.) and carbon disulphide (0.15 mL; 2.33 mmol; 10 equiv.) in dioxane (10 mL), as described above for the preparation of 2,2,2-tris[5-(2,3,4,6-tetra-O-acetyl-1-thio-β-D-mannopyranosyl)-2-oxapentyl]ethyl isothiocyanate. Thus 0.26 g (yield 80%) of a white solid is obtained having the following characteristics $[\alpha]_D$+61.90° (c 0.4; dichloromethane)
mass spectrum (FAB$^+$): m/z 1412 (100%, [M+Na]$^+$)

2. Preparation of Compound No. 5

This compound is obtained by condensation of compound No. 1 (20 mg; 11.1 μmol) and 2,2,2-tris[5-(2,3,4,6-tetra-O-acetyl-1-thio-β-D-glucopyranosyl)-2-oxapentyl]ethyl isothiocyanate (160 mg; 115 μmol; 1.5 equiv.) in water-acetone (1:2, 3 mL) at pH 8-9 (solid sodium hydrogen carbonate) followed by deacetylation as described above for the preparation of compound No. 4. After freeze-drying, compound No. 5 is obtained (56 mg, 68%) having the following characteristics:

$[\alpha]_D$–16.2° (c 1.0; water)
mass spectrum (MALDITOF): m/z 7751.88 ([M+H]$^+$)
solubility in water: 670 g.L$^{-1}$ (87 mmol.L$^{-1}$)
$^1$H NMR data (500 MHz, 343 K, D$_2$O): δ 5.46 (7H, bd, $J_{1,2}$ 3.0 Hz, H-1); 4.86 (21H, d, $J_{1',2'}$ 9.5 Hz, H-1'); 4.29 (7H, m, H-5); 4.28 (7H, m, H-3); 4.27 (21H, d, $J_{6a',6b'}$ 12.0 Hz, H-6a'); 4.13 (21H, d, H-6b'); 4.09 (14H, m, $CH_2N_{cyst}$); 4.07 (7H, m, H-2); 3.98 (42H, t, $^3J_{H,H}$ 6.5 Hz, H-3$_{Pent}$); 3.97 (7H, m, H-4); 3.89 (21H, t, $J_{2',3'}$=$J_{3',4'}$=9.3 Hz, H-3'); 3.84 (98H, m, H-4', H-5', $CH_2N_{branch}$, H-1$_{Pent}$); 3.73 (21H, t, H-2'); 3.65 (7H, m, H-6a); 3.38 (7H, m, H-6b); 3.32 (14H, bt, $^3J_{H,H}$=6.5 Hz, $CH_2S_{cyst}$); 3.22; 3.18 (42H, 2 dt, $J_{5a,5b}$ 13.0 Hz, $J_{4,5}$ 5.5 Hz, H-5$_{Pent}$); 2.33 (42H, m, H-4$_{Pent}$)
$^{13}$C NMR data (125.7 MHz; 343 K; D$_2$O): δ 181.4 (CS), 102.6 (C-1); 86.3 (C-1'); 85.1 (C-4); 80.5 (C-5'); 78.0 (C-3'); 73.4 (C-3); 73.2 (C-2'); 72.8 (C-2, C-5); 71.2 (C-1$_{Pent}$); 70.4 (C-3$_{Pent}$); 70.3 (C-4'); 61.8 (C-6'); 46.5 ($CH_2N_{cyst}$, $CH_2N_{branch}$); 45.0 (C$_q$); 34.2 (C-6); 33.1 ($CH_2S_{cyst}$); 30.0 (C-4$_{Pent}$); 27.4 (C-5$_{Pent}$)

Example 6

Preparation of heptakis[6-S-[2-N'-[2-[5-(1-thio-α-D-mannopyranosyl)-2-oxapentyl]-2,2-bis[5-(1-thio-β-D-glucopyranosyl)-2-oxapentyl]ethyl]thioureido]ethyl-6-thio]cyclomaltoheptaose (compound No. 6)

This compound corresponds to formula (V) given above with n=1, m=6, in which all the $R_1$s are identical and represent $CH_2$—$C[(CH_2OCH_2CH_2CH_2R_2)_2(CH_2OCH_2CH_2CH_2R_3)]$, X represents a hydrogen atom, $R_2$ and $R_3$ corresponding to the formulae (VI) and (III), respectively.

This compound is obtained by condensation of compound No. 1 (see Example 1) with 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl] ethyl isothiocyanate followed by a basic hydrolysis of the protective acetyl group.

1. Preparation of 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl]ethyl isothiocyanate This compound is prepared by carrying out the following stages:

a) Preparation of 2-(2-oxapent-4-enyl)-2,2-bis[5-(2,3,4,6-tetra-O-acetyl-1-thio-β-D-glucopyranosyl)-2-oxapentyl]ethanol A solution of tri-O-allylpentaerythritol (0.20 g; 0.78 mmol) and 2,3,4,6-tetra-O-acetyl-1-thio-β-D-glucopyranose (0.85 g; 2.34 mmol; 1 equiv.), in anhydrous methanol (15 mL) gas-free and under argon, is irradiated with ultraviolet light (250 nm) at ambient temperature for 6 hours. The solvent is evaporated and the residue is purified by silica gel column chromatography with ethyl acetate-petroleum ether 3:2. Thus 0.58 g (yield 76%) of a white solid is obtained, having the following characteristics:

$[\alpha]_D$ −26.6° (c 0.8; dichloromethane)
mass spectrum (FAB$^+$): m/z 1007 (100%, [M+Na]$^+$)

b) Preparation of 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl]ethanol A solution of 2-(2-oxapent-4-enyl)-2,2-bis[5-(2,3,4,6-tetra-O-acetyl-1-thio-β-D-glucopyranosyl)-2-oxapentyl]ethanol (0.53 g; 0.54 mmol) and 2,3,4,6-tetra-O-acetyl-1-thio-α-D-mannopyranose (0.29 g; 0.81 mmol; 1.5 equiv.), in anhydrous methanol (35 mL) gas-free and under argon, is irradiated with ultraviolet light (250 nm) at ambient temperature for 6 hours. The solvent is evaporated and the residue is purified by silica gel column chromatography with ethyl acetate-petroleum ether 3:1. Thus 0.55 g (yield 76%) of a white solid is obtained, having the following characteristics:

$[\alpha]_D$ +15.50° (c 1.0; dichloromethane)
mass spectrum (FAB$^+$): m/z 1371 (100%, [M+Na]$^+$)

c) Preparation of 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl]ethyl azide This compound is obtained from 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl]ethanol (0.43 g; 0.32 mmol) by reaction with trifluoromethanesulphonic anhydride followed by treatment with sodium azide as described above for the preparation of 2,2,2-tris[5-(2,3,4,6-tetra-O-acetyl-1-thio-α-D-mannopyranosyl)-2-oxapentyl]ethyl azide. Thus 0.33 g of a white solid is obtained (yield 75%) having the following characteristics:

$[\alpha]_D$ +8.20° (c 1.0; dichloromethane)
mass spectrum (FAB$^+$): m/z 1396 (100%, [M+Na]$^+$)

d) Preparation of 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl]ethyl isothiocyanate This compound is obtained by isothiocyanation of 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl]ethyl azide (0.25 g; 0.18 mmol) by treatment with triphenylphosphine (52 mg; 0.20 mmol; 1.1 equiv.) and carbon disulphide (0.11 mL; 1.80 mmol; 10 equiv.) in dioxane (8 mL), as described above for the preparation of 2,2,2-tris[5-(2,3,4,6-tetra-O-acetyl-1-thio-β-D-mannopyranosyl)-2-oxapentyl]ethyl isothiocyanate. Thus 0.20 g (yield 80%) of a white solid is obtained having the following characteristics:

$[\alpha]_D$ +9.7° (c 1.0; dichloromethane)
mass spectrum (FAB$^+$): m/z 1412 (100%, [M+Na]$^+$)

2. Preparation of Compound No. 6

This compound is obtained by condensation of compound No. 1 (20 mg; 11.1 μmol) with 2-[5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl] ethyl isothiocyanate (160 mg; 115 μmol; 1.5 equiv.) in water-acetone (1:2, 3 mL) at pH 8-9 (solid sodium hydrogen carbonate) followed by deacetylation as described above for the preparation of compound No. 4. After freeze-drying, compound No. 6 is obtained (48 mg, 60%) having the following characteristics:

$[\alpha]_D$ +25.0° (c 1.0; water)
mass spectrum (MALDITOF): m/z 7751.88 ([M+H]$^+$)
solubility in water: 700 g.L$^{-1}$ (91 mmol.L$^{-1}$)

$^1$H NMR data (500 MHz, 353 K, D$_2$O): δ 5.87 (7H, s, H-1'$_{Man}$); 5.60 (7H, bd, J$_{1,2}$ 3.5 Hz, H-1); 5.00 (14H, d, J$_{1', 2'}$ 10.0 Hz, H-1'$_{Glc}$); 4.57 (7H, m, m, H-2'$_{Man}$); 4.42 (7H, m, H-5'$_{Man}$); 4.41 (7H, m, H-5); 4.39 (14H, d, J$_{6a', 6b'}$ 12.0 Hz, H-6a'$_{Glc}$); 4.38 (7H, m, H-3); 4.36 (21H, m, H-3'$_{Man}$, H-6a'$_{Man}$, H-6b'$_{Man}$); 4.29 (7H, m, H-4'$_{Man}$); 4.25 (14H, dd, J$_{5', 6b'}$ 4.5 Hz, H-6b'$_{Glc}$); 4.22 (14H, m, CH$_2$N$_{cyst}$); 4.17 (7H, d, H-2); 4.09 (42H, t, J$_{3,4}$ 5.5 Hz, H-3$_{Pent}$); 4.08 (7H, m, H-4); 4.02 (14H, t, J$_{2', 3'}$=J$_{3', 4'}$ 9.4 Hz, H-3'$_{Glc}$); 3.96 (84H, m, H-4'$_{Glc}$, H-5'$_{Glc}$, CH$_2$NH$_{branch}$, H-1$_{Pent}$); 3.85 (14H, t, J$_{1', 2'}$ 9.4 Hz, H-2'$_{Glc}$); 3.78 (7H, m, H-6a); 3.51 (7H, m, H-6b); 3.46 (14H, bt, $^3$J$_{H, H}$ 6.5 Hz, CH$_2$S$_{cyst}$); 3.34; 3.32 (42H, 2 dt, J$_{5a, 5b}$ 13.0 Hz, J$_{4,5}$ 6.0 Hz, H-5$_{Pent}$); 2.45 (42H, m, H-4$_{Pent}$)

$^{13}$C NMR data (125.7 MHz; 353 K; D$_2$O): δ 181.9 (CS); 102.8 (C-1); 86.3 (C-1'$_{Glc}$); 86.0 (C-1'$_{Man}$); 85.3 (C-4); 80.7 (C-5'$_{Glc}$); 78.3 (C-3'$_{Glc}$); 74.1 (C-5'$_{Man}$); 73.6 (C-3); 73.4 (C-2'$_{Glc}$); 73.0 (C-2, C-5); 72.8 (C-2'$_{Man}$); 72.3 (C-3'$_{Man}$); 71.4 (C-1$_{Pent}$); 71.0 (C-3$_{Pent}$); 70.6 (C-4'$_{Glc}$); 67.9 (C-4'$_{Man}$); 62.0 (C-6'$_{Glc}$); 61.7 (C-6'$_{Man}$); 45.1 (C$_q$); 45.0 (CH$_2$N$_{cyst}$, CH$_2$N$_{branch}$); 34.5 (C-6); 33.3 (CH$_2$S$_{cyst}$); 30.4; 30.0 (C-4$_{Pent}$); 28.7; 27.6 (C-5$_{Pent}$)

Example 7

Preparation of heptakis[6-S-[2-N'-[2,2-bis[5-(1-thio-α-D-mannopyranosyl)-2-oxapentyl]-2-[5-(1-thio-β-D-glucopyranosyl)-2-oxapentyl]ethyl]thioureido]ethylthio]cyclomaltoheptaose (compound No. 7)

This compound corresponds to formula (V) given above with n=1, m=6, in which all the R$_1$s are identical and represent CH$_2$—C[(CH$_2$OCH$_2$CH$_2$CH$_2$R$_2$)$_2$(CH$_2$OCH$_2$CH$_2$CH$_2$R$_3$)], X represents a hydrogen atom, R$_2$ and R$_3$ corresponding to formulae (III) and (VI), respectively.

This compound is obtained by condensation of compound No. 1 (see Example 1) with 2,2-bis[5-(2,3,4,6-tetra-O-acetyl-1-thio-α-D-mannopyranosyl)-2-oxapentyl]-2-[5-(2,3,4,6-tetra-O-acetyl-1-thio-β-D-glucopyranosyl)-2-oxapentyl]ethyl isothiocyanate followed by an alkaline hydrolysis of the protective acetyl group.

1. Preparation of 2,2-bis[5-(2,3,4,6-tetra-O-acetyl-1-thio-α-D-mannopyranosyl)-2-oxapentyl]-2-[5-(2,3,4,6-tetra-O-acetyl-1-thio-β-D-glucopyranosyl)-2-oxapentyl]ethyl isothiocyanate This compound is prepared with the following stages:

a) Preparation of 2-(2-oxapent-4-enyl)-2,2-bis[5-(2,3,4,6-tetra-O-acetyl-1-thio-α-D-mannopyranosyl)-2-oxapentyl]ethanol A solution of tri-O-allylpentaerythritol (0.20 g, 0.78 mmol) and 2,3,4,6-tetra-O-acetyl-1-thio-α-D-mannopyranose (0.85 g; 2.34 mmol; 1 equiv.) in anhydrous methanol (15 mL), gas-free and under argon, is irradiated with ultraviolet light (250 nm) at ambient temperature for 6 hours. The solvent is evaporated and the residue is purified by silica gel column chromatography with the ethyl acetate-petroleum ether 1:1. Thus 0.55 g (yield 72%) of a white solid is obtained, having the following characteristics:

$[α]_D$+20.20° (c 0.8; dichloromethane)
mass spectrum (FAB$^+$): m/z 1007 (100%, [M+Na]$^+$)

b) Preparation of 2,2-bis[5-(2,3,4,6-tetra-O-acetyl-1-thio-α-D-mannopyranosyl)-2-oxapentyl]-2-[5-(2,3,4,6-tetra-O-acetyl-1-thio-β-D-glucopyranosyl)-2-oxapentyl]ethanol A solution of 2-(2-oxapent-4-enyl)-2,2-bis[5-(2,3,4,6-tetra-O-acetyl-1-thio-α-D-mannopyranosyl)-2-oxapentyl]ethanol (0.49 g; 0.49 mmol) and 2,3,4,6-tetra-O-acetyl-1-thio-β-D-glucopyranose (0.27 g; 0.66 mmol; 1.5 equiv.), in anhydrous methanol (25 mL) gas-free and under argon, is irradiated with ultraviolet light (250 nm) at ambient temperature for 6 hours. The solvent is evaporated and the residue is purified by silica gel column chromatography with ethyl acetate-petroleum ether 3:1. Thus 0.42 g (yield 64%) of a white solid is obtained, having the following characteristics:

$[α]_D$+29.40° (c 0.6; dichloromethane)
mass spectrum (FAB$^+$): m/z 1371 (100%, [M+Na]$^+$)

c) Preparation of 2,2-bis[5-(2,3,4,6-tetra-O-acetyl-1-thio-α-D-mannopyranosyl)-2-oxapentyl]-2-[5-(2,3,4,6-tetra-O-acetyl-1-thio-β-D-glucopyranosyl)-2-oxapentyl]ethyl azide This compound is obtained from 2,2-bis[5-(2,3,4,6-tetra-O-acetyl-1-thio-α-D-mannopyranosyl)-2-oxapentyl]-2-[5-(2,3,4,6-tetra-O-acetyl-1-thio-β-D-glucopyranosyl)-2-oxapentyl]ethanol (0.688 g; 0.51 mmol), by reaction with trifluoromethanesulphonic anhydride followed by treatment with sodium azide as described above for the preparation of 2,2,2-tris[5-(2,3,4,6-tetra-O-acetyl-1-thio-α-D-mannopyranosyl)-2-oxapentyl]ethyl azide. Thus 0.554 g of a white solid is obtained (yield 79%) having the following characteristics:

$[α]_D$+45.3° (c 1.0; dichloromethane)
mass spectrum (FAB$^+$): m/z 1396 (100%, [M+Na]$^+$)

d) Preparation of 2,2-bis [5-(2,3,4,6-tetra-O-acetyl-1-thio-α-D-mannopyranosyl)-2-oxapentyl]-2-[5-(2,3,4,6-tetra-O-acetyl-1-thio-β-D-glucopyranosyl)-2-oxapentyl]ethyl isothiocyanate This compound is obtained by isothiocyanation of 2,2-bis [5-(2,3,4,6-tetra-O-acetyl-1-thio-α-D-mannopyranosyl)-2-oxapentyl]-2,2-bis[5-(2,3,4,6-tetra-O-acetyl-1-thio-β-D-glucopyranosyl)-2-oxapentyl]ethyl azide (131 mg; 0.095 mmol) by treatment with triphenyiphosphine (28 mg; 0.10 mmol; 1.1 equiv.) and carbon disuiphide (60 μL; 0.95 mmol; 10 equiv) in dioxane (5 mL), as described above for the preparation of 2,2,2-tris[5-(2,3,4,6-tetra-O-acetyl-1-thio-β-D-mannopyranosyl)-2-oxapentyl]ethyl isothiocyanate. Thus 95 mg (yield 72%) of a white solid is obtained having the following characteristics:

$[α]_D$+40.80° (c 1.0; dichioromethane)
mass spectrum (FAB$^+$): m/z 1412 (100%, [M+Na]$^+$)

2. Preparation of Compound No. 7

This compound is obtained by condensation of compound No. 1(20 mg; 11.1 μmol) in water-acetone (1:2; 3 mL) with 2,2-bis[5-(2,3,4,6-tetra-O-acetyl-1-thio-α-D-mannopyranosyl)-2-oxapentyi]-2-[5-(2,3,4,6-tetra-O-acetyl-1-thio-β-D-glucopyranosyl)-2-oxapentyl]ethyl isothiocyanate (160 mg; 115 μmol; 1.5 equiv.), in water-acetone (1:2, 3 mL) at pH 8-9 (solid sodium hydrogen carbonate), followed by deacetylation as described above for the preparation of compound No. 4. After freeze-drying, compound No. 7 is obtained (40 mg, 52%) having the following characteristics:

$[α]_D$+66.00° (c 1.0; water)
mass spectrum (MALDITOF): m/z 7751.88 ([M+H]$^+$)
solubility in water: 800 g.L$^{-1}$ (103 mmol.L$^{-1}$)
$^1$H NMR data (500 MHz, 353 K, D$_2$O): δ 5.67 (14H, s, H-1'$_{Man}$); 5.47 (7H, bs, H-1); 4.86 (7H, d, $J_{1',\,2'}$ 10.0 Hz, H-1'$_{Glc}$); 4.43 (14H, m, H-2'$_{Man}$); 4.29 (21H, m, H-5'$_{Man}$, H-5); 4.26 (7H, m, H-3); 4.25 (7H, d, $J_{6a',\,6b'}$ 12.0 Hz, H-6a'$_{Glc}$); 4.14 (42H, m, H-3'$_{Man}$, H-6a'$_{Man}$, H-6b'$_{Man}$); 4.14 (14H, m, H-4'$_{Man}$); 4.09 (7H, d, H-6b'$_{Glc}$); 4.08 (14H, m, CH$_2$N$_{cyst}$); 4.04 (7H, d, H-2); 3.95 (49H, m, H-3$_{Pent}$, H-4); 3.85 (7H, t, $J_{2',\,3'}$=$J_{3',\,4'}$ 8.9 Hz, H-3'$_{Glc}$); 3.80 (70H, m, H-4'$_{Glc}$, H-5'$_{Glc}$, CH$_2$NH$_{branch}$, H-1$_{Pent}$); 3.71 (7H, t, H-2'$_{Glc}$); 3.61 (7H, m, H-6a); 3.37 (7H, m, H-6b); 3.32 (14H, m, CH$_2$S$_{cyst}$); 3.17; 3.12 (42H, 2 dt, $J_{5a,\,5b}$ 13.5 Hz, $J_{4,5}$ 6.5 Hz, H-5$_{Pent}$) 2.30 (42H, t, $J_{3,4}$ 6.5 Hz, H-4$_{Pent}$)
$^{13}$C NMR data (125.7 MHz, 353 K, D$_2$O): δ 182.0 (CS); 102.7 (C-1); 86.1 (C-1'$_{Glc}$); 85.7 (C-1'$_{Man}$); 85.2 (C-4); 80.9 (C-5'$_{Glc}$); 78.0 (C-3'$_{Glc}$); 73.9 (C-5'$_{Man}$); 73.1 (C-3); 73.0 (C-2'$_{Glc}$); 72.8 (C-2, C-5); 72.6 (C-2'$_{Man}$); 72.0 (C-3'$_{Man}$); 71.1 (C-1$_{Pent}$); 70.8 (C-3$_{Pent}$); 70.3 (C-4'$_{Glc}$); 67.7 (C-4'$_{Man}$); 61.8 (C-6'$_{Glc}$); 61.5 (C-6'$_{Man}$); 45.1 (CH$_2$N$_{cyst}$, CH$_2$N$_{branch}$); 45.0 (C$_q$); 34.2 (C-6); 33.1 (CH$_2$S); 30.2; 29.3 (C-4$_{Pent}$); 28.5; 27.5 (C-5$_{Pent}$)

Example 8

Evaluation of the Affinity of the Thioureidocysteaminyl-Cyclodextrin Compounds No. 2 to 7 for the Lectin Specific to Concanavalin A (ConA) Mannose The affinity of compounds No. 2 to 7 for the lectin specific to concanavalin A (ConA) mannose is evaluated according to the ELLA protocol. Thus the concentration of compounds No. 2 to 7 necessary for inhibiting 50% of the association of ConA with a reference ligand (yeast mannan in our case) fixed to the cell of a microtitre plate (IC$_{50}$) is obtained. The IC$_{50}$ values are inversely proportional to the respective affinities.

The cells of a microtitre plate (Nunc-Inmno™ plates, MaxiSorp™) are loaded with 100 μL of a stock solution of yeast mannan (Sigma, 10 μg.mL$^{-1}$) in a saline phosphate buffer solution (PBS; pH 7.3 containing Ca$^{2+}$ 0.1 mM and Mn$^{2+}$ 0.1 mM) for one night at ambient temperature. The cells are washed (3×300 μL) with a buffer solution containing 0.05% (v/v) of Tween 20 (PBST). This washing protocol is repeated after each incubation during the test. A bovine serum albumin solution (BSA, 1%) in PBS (150 μL/cell) is then added to the cells followed by incubation for 1 hour at 37° C., then washed.

In order to determine the optimal lectin concentration for inhibition studies, 100 μL of a series of concanavalin A solutions marked with radish peroxidase of 10$^{-1}$ to 10$^{-5}$ mg mL$^{-1}$ in PBS is added to the cells loaded with mannan, and treated as indicated above. After incubation at 37° C. for 1 hour, the plates are washed (PBST) and a solution (50 μL) of the diammonium salt of 2,2'-azinobis(3-ethylbenzothiazoline-6-sulphonic) acid (ABTS, 1 mg in 4 mL) in citrate buffer (0.2 M, pH 4.0 with 0.015% hydrogen peroxide) is added. The reaction is stopped after 20 minutes by adding 50 μL/cell of sulphuric acid 1 M and the absorbances are measured at 415 nm using an ELISA reader. The control cells contained citrate-phosphate buffer. The lectin concentration marked with peroxidase giving an absorbance value of between 0.8 and 1.0 (typically between $10^{-2}$ and $10^{-3}$ mg.mL$^{-1}$) was used in the inhibition tests.

For the inhibition tests, stock solutions of compounds No. 2 to 7 were used at a concentration of 5 to 7 mg.mL$^{-1}$ in PBS. In a series of experiments, ConA marked with radish peroxidase in an appropriate concentration as indicated above (60 μL/cell) is added to the solutions of each compound (60 μL/cell) in PBS sequentially diluted twice, in a Nunclon™ (Delta) microtitre plate which is incubated at 37° C. for 1 hour. The solutions (100 μL/cell) are then transferred onto a microtitre plate loaded with mannan and treated as indicated above, which is then incubated at 37° C. for 1 hour. The cells are washed (PBST) and the ABTS solution (50 μL/cell) is added. After 20 minutes, the reaction is stopped (sulphuric acid) and the absorbances are measured. The percentage of inhibition is calculated with the formula:

$$\% \text{ d'inhibition} = \frac{A_{in\ the\ absence\ of\ inhibitor}}{A_{in\ the\ presence\ of\ inhibitor}} \times 100$$

In Table 1 below, the IC$_{50}$ values for compounds No. 2 to 7 are given (average of three independent experiments) compared with the corresponding value for methyl-α-D-glucopyranoside, used as monovalent reference ligand. A substantial increase in the affinity for lectin is observed in the case of the hyperbranched derivatives comprising mannopyranosyl substituents.

TABLE 1

ELLA data for inhibition of the association between the yeast mannan and the ConA lectin marked with radish peroxidase.

| | Compound | | | | | | |
|---|---|---|---|---|---|---|---|
| | Me-α-D-Glcp | No. 2 | No. 3 | No. 4 | No. 5 | No. 6 | No. 7 |
| IC$_{50}$ (μM) | 865 | 175 | 21 | 5 | n.i.$^a$ | 18 | 13 |
| Relative affinity | 1 | 4.9 | 41 | 173 | — | 48 | 67 |
| Relative molar affinity | 1 | 0.7 | 2.0 | 8.2 | — | 6.9 | 4.8 |

$^a$No significant inhibition detected at a concentration of 5 mM.

FIG. 1 represents the variation in the inhibition of the association between ConA lectin and yeast mannan by compounds No. 2, No. 3, No. 4, No. 6 and No. 7, of the thioureidocysteaminyl-cyclodextrin type, as well as for heptakis(6-deoxy-6-α-D-mannopyranosylthioureido)cyclomaltoheptaose, a heptavalent derivative of the thioureido-cyclodextrin type described in the document *ChemBioChem* 2001, as a function of the concentration of the mannosyl ligand. A comparison of the curves for compound No. 2 and for the derivative of per-(C-6)-amine shows a remarkable increase in the affinity for lectin as a result of the introduction of the cysteaminyl spacer. A much greater increase in the affinity is observed moreover when the mannopyranosyl ligands are incorporated into a structure of the hyperbranched type (see curves for compounds No. 3, No. 4, No. 6 and No. 7).

Thus, the concentration of compound No. 2 necessary for inhibiting 50% of the association between concanavalin A and the yeast mannan fixed to the microplate (IC$_{50}$), is 175 μM, whereas for heptakis(6-deoxy-6-α-D-mannopyranosylthioureido)cyclomaltoheptaose, a heptavalent derivative of the thioureido-cyclodextrin type, the inhibition at the same concentration is only 8% of the preceding value. The effectiveness of the recognition phenomenon is also much higher for hyperbranched thioureidocysteaminyl-cyclodextrins. Thus, the IC$_{50}$ values for compounds No. 3, No. 4, No. 6 and No. 7 are comprised between 5 and 21 μM, i.e. between one and two orders of magnitude lower than the value found for compound No. 2. At the same time, the selectivity in recognition between the glucidic marker placed on cyclodextrin and the specific lectin remains intact. Thus, compound No. 6 which only comprises β-D-glucopyranosyl substituents, is not recognized by ConA, a lectin specific to the α-D-mannopyranosyl ligand. No non-specific recognition phenomena caused by the presence of cyclodextrin are observed.

Example 9

Inclusion of Taxotere in heptakis[6-S-(2-aminoethyl-6-thio)]cyclomaltoheptaose heptahydrochloride (compound No. 1)

Starting with Taxotere in the pure state, 2.1 mg (2.47 mmol) of this product is dispersed in 1 mL of a solution containing 50 mmol.L$^{-1}$ of compound No. 1 in sterile water, then the suspension obtained is stirred at 70° C. until a clear solution is obtained which indicates the complexing of the Taxotere. Once formed, the complex remains in solution at ambient temperature. Thus an increase in the solubility of the Taxotere (2.1 g.L$^{-1}$) is obtained of the order of 525 times that of the Taxotere in the absence of cyclodextrin (0.004 g.L$^{-1}$).

Example 10

Inclusion of Taxotere in heptakis[6-S-[2-N'-[2,2,2-tris[5-(1-thio-α-D-mannopyranosyl)-2-oxapentyl]ethyl]thioureido]ethyl-6-thio]cyclomaltoheptaose (compound No. 4)

Starting with Taxotere in the pure state, 0.2 mg (235 μmol) of this product is dispersed in 0.1 mL of a solution containing 50 mmol.L$^{-1}$ of compound No. 4 in sterile water, the suspension obtained is then stirred at 70° C. until a clear solution is obtained which indicates the encapsulation of the Taxotere. Once formed, the complex remains in solution at ambient temperature. Thus an increase in the solubility of the Taxotere (2.0 g.L$^{-1}$) is obtained of the order of 500 times that of the Taxotere in the absence of cyclodextrin.

The invention claimed is:

1. A process for the preparation of a compound of formula (I)

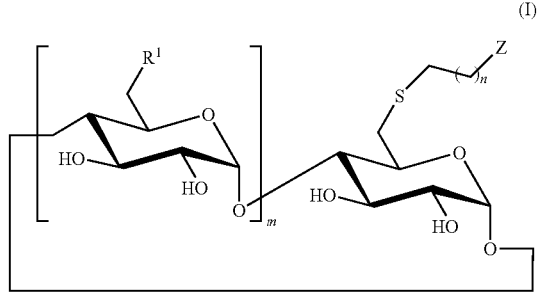

in which:
n represents an integer from 1 to 6;
m represents an integer equal to 5, 6 or 7;
$R^1$ represents either an OH group or an —S—CH$_2$—(CH$_2$)$_n$—Z group, the $R^1$ groups all being identical;
Z represents a

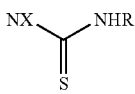

group,
X representing a hydrogen atom or an alkyl group comprising from 1 to 6 carbon atoms and
R representing a biorecognition element comprising an amino acid derivative, a peptide, a monosaccharide, an oligosaccharide, a multiplication element with several branchings comprising glucidic groups which can be identical or different, or a visualization probe or fluorescent or radioactive detection probe,
said multiplication element with several branchings consisting of tris(2-hydroxymethyl)methyl radical or pentaerythritol radical, said tris(2-hydroxymethyl) radical being linked to the group Z by the quaternary carbon radical, and the pentaerythritol radical being linked to the group Z by a primary carbon radical,
said process comprising the following stages:
reacting a compound selectively or totally halogenated in primary alcohol position, of the following formula (VII):

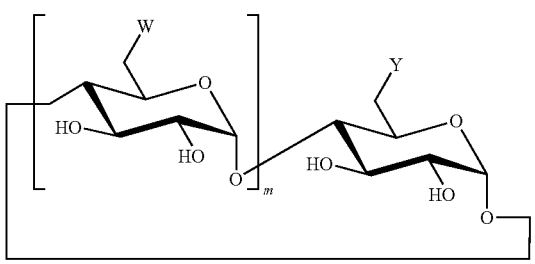

(VII)

m being as defined above,
and Y representing a halogen atom chosen from the group consisting of chlorine, bromine, and iodine, with an ω-aminoalkanethiol of the following formula (VIII):

(VIII)

said ω-aminoalkanethiol optionally being N-alkylated,
or the corresponding salt of the following formula (VIII-a):

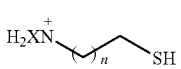

(VIII-a)

said salt being associated with a halide counter ion,
n and X being as defined above,
in order to obtain a compound of formula (I) as defined above and having the following formulae (A-a):

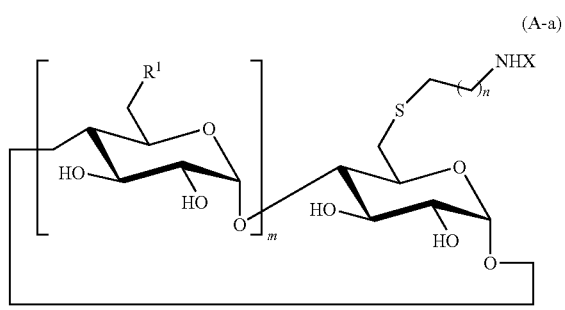

(A-a)

and
the reaction of the compound of formula (A-a) as obtained in the preceding stage with an isothiocyanate of the following formula (IX):

in which R is as defined above,
in order to obtain a compound of formula (I) as defined above, and corresponding to the following formula:

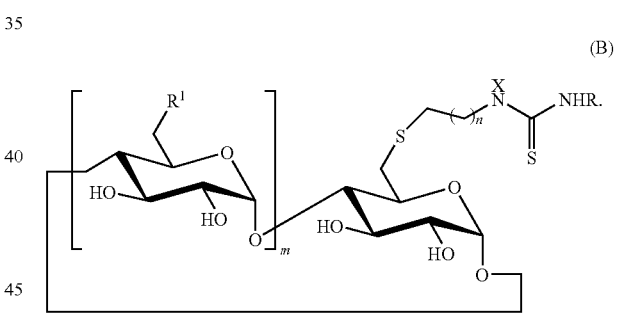

(B)

2. The preparation process according to claim 1 of a compound having the following general formula (I-b):

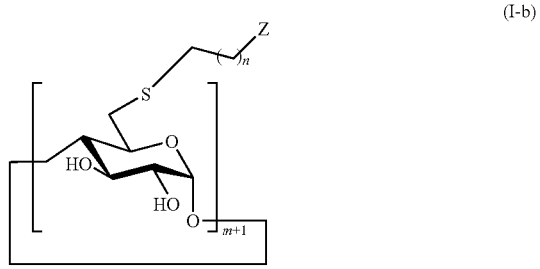

(I-b)

said process comprising the following stages:
reacting a per(6-deoxy-6-halo) cyclodextrin compound, of the following formula (VII-a):

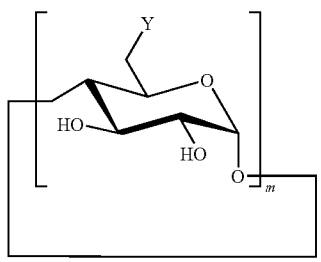
(VII-a)

with an ω-aminoalkanethiol of the following formula (VIII):

(VIII)

said ω-aminoalkanethiol being N-alkylated,
or the corresponding salt of the following formula (VIII-a):

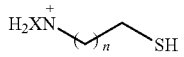
(VIII-a)

said salt being associated with a halide counter ion,
and X being a hydrogen atom,
the compound of formula (VIII) being cysteamine of formula $H_2N-CH_2-CH_2-SH$,
in order to obtain a compound of the following formula (I-c),

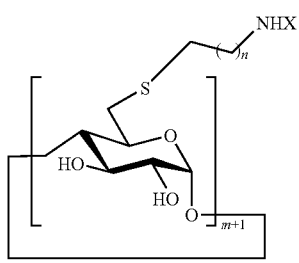
(I-c)

and
the reaction of the compound of formula (I-c) as obtained in the preceding stage with an isothiocyanate of the following formula (IX):

$R-N=C=S$ (IX)

in order to obtain a compound of the following formula (II) or (II-a)

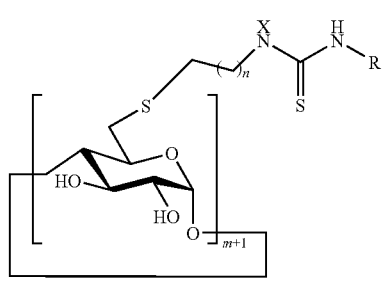
(II)

(II-a)

3. The preparation process according to claim 1 of compounds having the following formula:

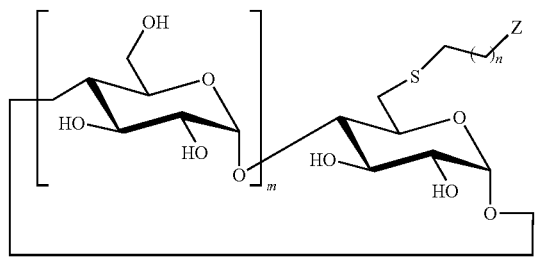
(I-a)

said process comprising the following stages:
reacting a compound selectively halogenated in primary alcohol position, of the following formula (VII):

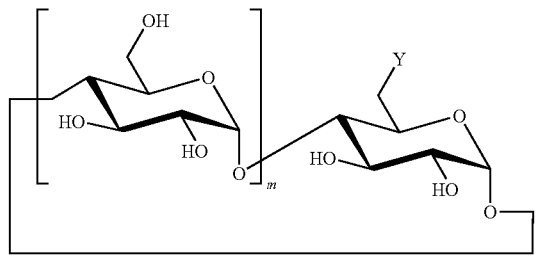
(VII)

with an ω-aminoalkanethiol of the following formula (VIII):

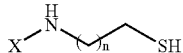
(VIII)

said ω-aminoalkanethiol optionally being N-alkylated, or the corresponding salt of the following formula (VIII-a):

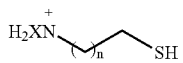
(VIII-a)

said salt being associated with halide as a counter ion, and preferably being the chloride ion,
and X being a hydrogen atom,
the compound of formula (VIII) being cysteamine of formula $H_2N—CH_2—CH_2—SH$,
in order to obtain a compound of formula (I-f) of the following formula:

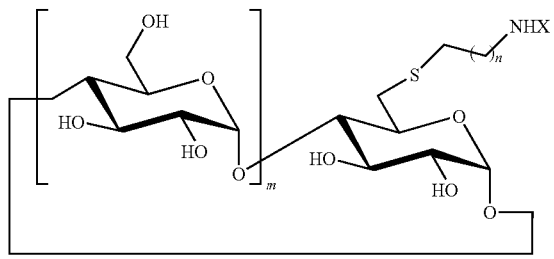
(I-f)

and
reacting the compound of formula (I-f) as obtained in the preceding stage with an isothiocyanate of the following formula (IX):

  R—N=C=S  (IX)

in order to obtain a compound of formula (I-h):

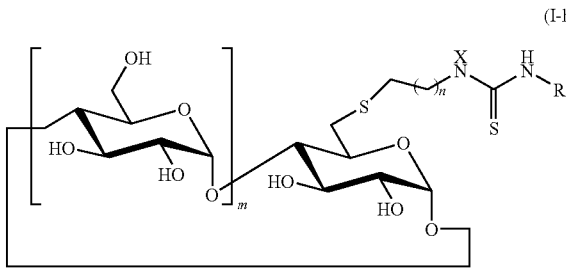
(I-h)

4. A compound of the following general formula:

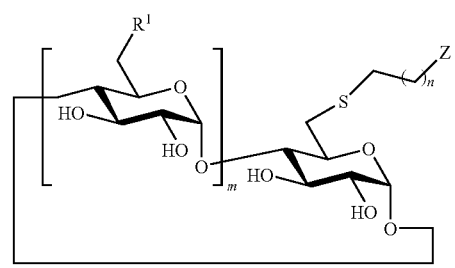
(I)

in which:
n represents an integer from 1 to 6;
m represents an integer equal to 5, 6 or 7;
$R^1$ represents either an OH group or an —S—CH$_2$—(CH$_2$)$_n$—Z group, the $R^1$ groups all being identical;
Z represents a

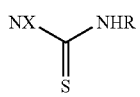

group,
X representing a hydrogen atom or an alkyl group comprising from 1 to 6 carbon atoms, and
R representing a biorecognition element comprising an amino acid derivative, a peptide, a monosaccharide, an oligosaccharide, a multiplication element with several branchings comprising glucidic groups which can be identical or different, or a visualization probe or fluorescent or radioactive detection probe,
said multiplication element with several branchings consisting of tris(2-hydroxymethyl)methyl radical or pentaerythritol radical, said tris(2-hydroxymethyl) radical being linked to the group Z by the quaternary carbon radical, and the pentaerythritol radical being linked to the group Z by a primary carbon radical.

5. The compound of claim 4, wherein $R^1$ represents OH, and having the following general formula:

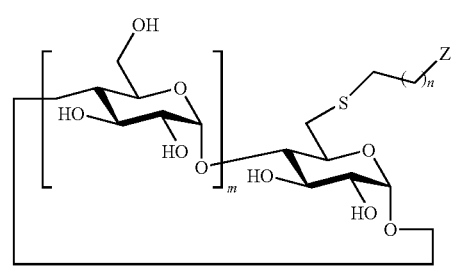
(I-a)

6. The compound of claim 4, wherein $R^1$ represents OH, having the formula (I-a)

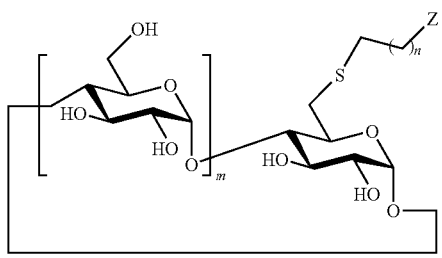
(I-a)

and Z represents a

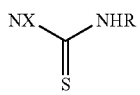

group, X being a hydrogen atom.

7. The compound of claim 4, wherein $R^1$ represents an —S—CH$_2$—(CH$_2$)$_n$—Z group, and having the following general formula:

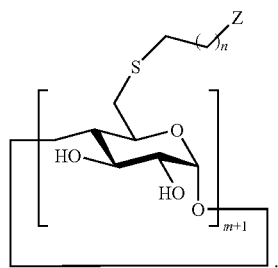
(I-b)

8. The compound of claim 7, wherein Z represents a

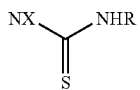

group,
X represents a hydrogen atom and n is equal to 1, and having the following formula:

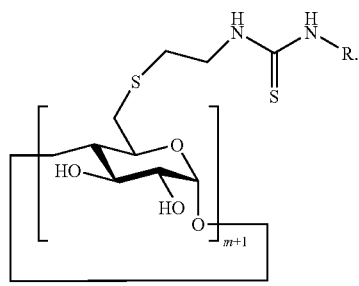
(II-a)

9. The compound according to claim 4, wherein $R^1$ represents an —S—CH$_2$—(CH$_2$)$_n$—Z group, Z represents a

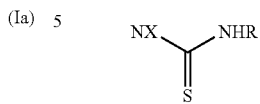

group, X represents a hydrogen atom, n is equal to 1, and the R group is chosen from the following groups:

the α-D-mannopyranosyl group, of the following formula (III):

(III)

the β-lactosyl group, of the following formula (III-a):

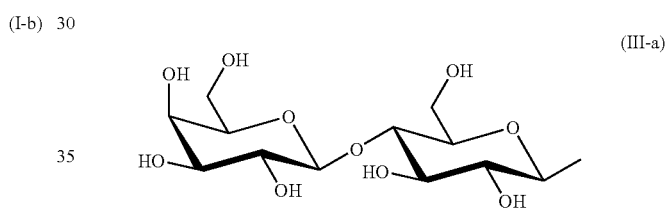
(III-a)

the group derived from Lewis X trisaccharide or from sialyl Lewis X tetrasaccharide, of the following formulae (III-b) and (III-c) respectively:

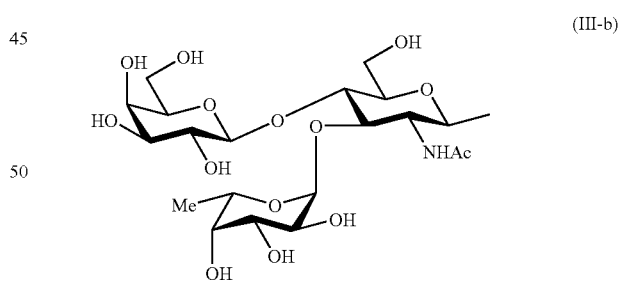
(III-b)

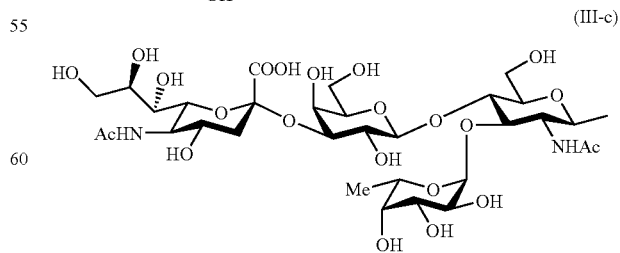
(III-c)

an oligosaccharide derived from heparin, of the following formula (III-d):

(III-d)

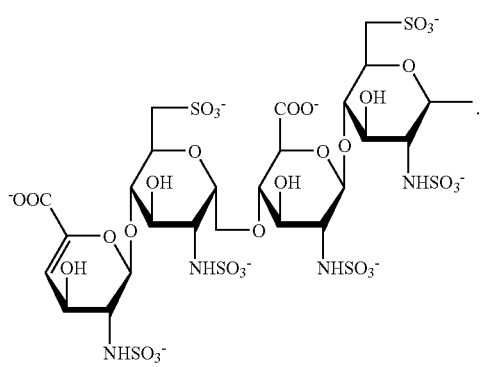

10. The compound of claim 4, wherein $R^1$ represents an —S—CH$_2$—(CH$_2$)$_n$—Z group, Z represents a

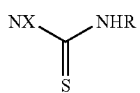

group, X represents a hydrogen atom, n is equal to 1, and:
R comprises a branching element consisting in a tris(2 hydroxymethyl)methyl radical, or
R represents one of the following groups:
the tris(α-D-mannopyranosyloxymethyl)methyl group, of the following formula (IV):

(IV)

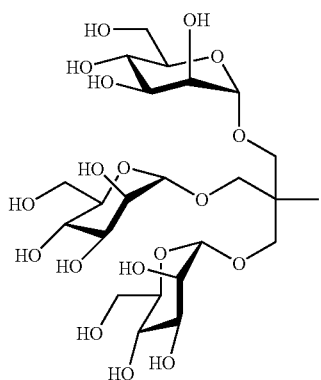

the tris(β-lactosyloxymethyl)methyl group, of the following formula (IV-a):

(IV-a)

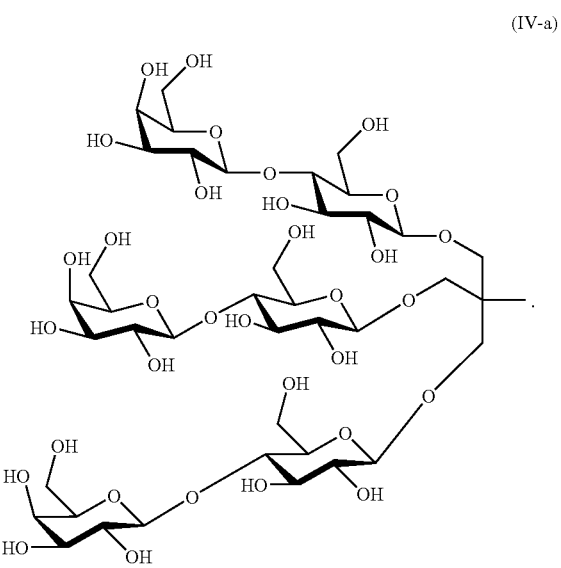

11. The compound of claim 4, wherein Z represents a

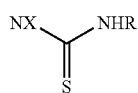

group, wherein R comprises a branching element derived from pentaerythritol, said compound having the following formula:

(V)

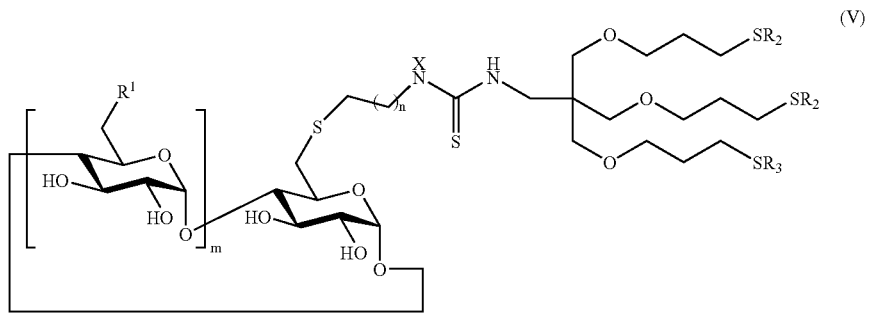

in which R² and R³ represent glucidic derivatives which can be different or identical or also a fluorescent or radioactive probe.

12. The compound of claim 11, wherein R¹ represents OH.

13. The compound of claim 11, wherein R¹ represents formula:

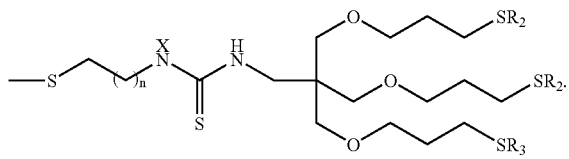

14. The compound of claim 11, wherein n is equal to 1, X represents a hydrogen atom and R² and R³ represent one of the following groups:

the α-D-mannopyranosyl group, of the following formula (III):

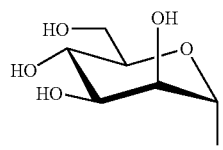

(III)

the β-lactosyl group, of the following formula (III-a):

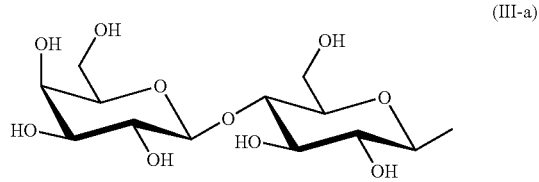

(III-a)

the β-D-glucopyranosyl group, of the following formula (VI):

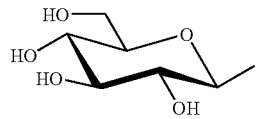

(VI)

R² and R³ being able to be identical or different.

15. The compound of claim 4, wherein m is equal to 6.

16. An inclusion complex of a compound according to claim 4 with a pharmacologically active molecule, a molar ratio between the compound and the pharmacologically active molecule being approximately 50:1 to approximately 1:1.

17. An inclusion complex of a compound according to claim 4 with a pharmacologically active molecule, a molar ratio between the compound the pharmacologically active molecule being approximately 50:1 to approximately 1:1, wherein the pharmacologically active molecule is an antineoplastic agent, belonging to the taxol family.

18. A pharmaceutical composition comprising a compound according to claim 4 with a pharmacologically acceptable vehicle.

19. A pharmaceutical composition comprising an inclusion complex of a compound according to claim 4, with a pharmacologically active molecule, a molar ratio between the compound and the pharmacologically active molecule being approximately 50:1 to approximately 1:1, in association with a pharmacologically acceptable vehicle.

20. A pharmaceutical composition comprising a compound according to claim 4 with a pharmacologically acceptable vehicle, in the form of an aqueous solution.

21. A pharmaceutical composition comprising an inclusion complex of a compound according to claim 4 with a pharmacologically active molecule, a molar ratio between the compound and the pharmacologically active molecule being approximately 50:1 to approximately 1:1, in association with a pharmacologically acceptable vehicle, the pharmacological compound being in the form of an aqueous solution.

22. A pharmaceutical composition comprising a compound according to claim 4 with a pharmacologically acceptable vehicle, wherein the composition contains per single dose approximately 50 mg to approximately 500 mg of the compound.

23. A pharmaceutical composition comprising an inclusion complex of a compound according to claim 4 with a pharmacologically active molecule, a molar ratio between the compound and the pharmacologically active molecule being approximately 50:1 to approximately 1:1, in association with a pharmacologically acceptable vehicle, wherein the composition contains per single dose approximately 100 mg to approximately 750 mg of one of said complex.

* * * * *

UNITED STATES PATENT AND TRADEMARK OFFICE
CERTIFICATE OF CORRECTION

PATENT NO.       : 7,632,941 B2                                              Page 1 of 1
APPLICATION NO. : 10/551343
DATED            : December 15, 2009
INVENTOR(S)      : Defaye et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 167 days.

Signed and Sealed this

Twenty-first Day of December, 2010

David J. Kappos
*Director of the United States Patent and Trademark Office*